(12) United States Patent
Peeters et al.

(10) Patent No.: US 10,511,827 B2
(45) Date of Patent: Dec. 17, 2019

(54) ADAPTABLE INSPECTION UNIT FOR EXISTING PROCESSING LINES

(71) Applicant: Qcify Inc, San Mateo, CA (US)

(72) Inventors: Raf Peeters, San Mateo, CA (US); Bert Peelaers, Herentals (BE); Bert Switten, Sacramento, CA (US)

(73) Assignee: Qcify Inc., San Mateo, CA (US)

( * ) Notice: Subject to any disclaimer, the term of this patent is extended or adjusted under 35 U.S.C. 154(b) by 0 days.

(21) Appl. No.: 16/257,039

(22) Filed: Jan. 24, 2019

(65) Prior Publication Data

US 2019/0174119 A1    Jun. 6, 2019

Related U.S. Application Data

(63) Continuation-in-part of application No. 16/031,956, filed on Jul. 10, 2018, now Pat. No. 10,257,496.
(Continued)

(51) Int. Cl.
| | |
|---|---|
| *H04N 13/243* | (2018.01) |
| *H04N 5/232* | (2006.01) |
| *G06T 7/00* | (2017.01) |
| *H04N 5/225* | (2006.01) |
| *G01N 21/84* | (2006.01) |
| *G01N 21/95* | (2006.01) |
| *H04N 13/254* | (2018.01) |

(52) U.S. Cl.
CPC .......... *H04N 13/243* (2018.05); *G01N 21/84* (2013.01); *G01N 21/95* (2013.01); *G06T 7/0004* (2013.01); *G06T 7/0008* (2013.01); *H04N 5/2256* (2013.01); *H04N 5/23203* (2013.01); *G01N 2021/845* (2013.01); *G06T 2207/10021* (2013.01); *G06T 2207/30128* (2013.01); *H04N 13/254* (2018.05)

(58) Field of Classification Search
None
See application file for complete search history.

(56) References Cited

U.S. PATENT DOCUMENTS

| | | | | |
|---|---|---|---|---|
| 2005/0226489 | A1* | 10/2005 | Beach | G06T 7/0004 382/141 |
| 2007/0295911 | A1* | 12/2007 | Sved | G01T 3/00 250/359.1 |

(Continued)

*Primary Examiner* — Eileen M Adams
(74) *Attorney, Agent, or Firm* — Imperium Patent Works LLP; Mark D. Marrello

(57) ABSTRACT

An adaptable inspection unit includes an attachment mechanism, an inspection sensor device, a data port that is capable of transmitting information, and a power port that is connectable to a power source, all of which are physically connected together. The adaptable inspection unit also includes a memory circuit and a processor circuit. The processing circuit controls the inspection sensor device and writes information transmitted via the data port. The attachment mechanism is a mounting bracket, a mounting bracket receptacle, a weldable material, a clamp, an adhesive, a magnet, a latch, a lock, a locating pin, a rail, a slide, locking pin, a bolt, a screw, gravity or friction. The attachment mechanism is used to connect the adaptable inspection unit to a processing line such that the adaptable inspection unit is capable of capturing an image of a sample traveling along the processing line.

14 Claims, 37 Drawing Sheets

IN-FLIGHT 3D INSPECTOR FRONT PERSPECTIVE VIEW

Related U.S. Application Data which is a continuation-in-part of application No. 15/995,126, filed on Jun. 1, 2018, now Pat. No. 10,298,909, which is a continuation of application No. 15/817,240, filed on Nov. 19, 2017, now Pat. No. 10,021,370, which is a continuation-in-part of application No. 15/219,870, filed on Jul. 26, 2016, now Pat. No. 10,021,369.

(56) References Cited

U.S. PATENT DOCUMENTS

2013/0188012 A1\* 7/2013 Bellis .................... H04N 5/2252
                                                            348/42
2017/0054950 A1\* 2/2017 Yeo ........................ H04N 7/188

\* cited by examiner

IN-FLIGHT 3D INSPECTOR FRONT PERSPECTIVE VIEW

IN-FLIGHT 3D INSPECTOR REAR PERSPECTIVE VIEW

IN-FLIGHT 3D INSPECTOR RIGHT SIDE VIEW

IN-FLIGHT 3D INSPECTOR LEFT SIDE VIEW

SAMPLE TRAVEL PATH THROUGH IN-FLIGHT 3D INSPECTOR

DOUBLE STEREO CAMERA SYSTEM CONFIGURATION

IMAGE OF SAMPLE CAPTURED BY THE FIRST CAMERA

IMAGE OF SAMPLE CAPTURED BY THE SECOND CAMERA

IMAGE OF SAMPLE CAPTURED BY THE THIRD CAMERA

IMAGE OF SAMPLE CAPTURED BY THE FOURTH CAMERA

IN-FLIGHT 3D INSPECTOR WITH DEFECT PROCESSING FLOWCHART

INSPECTION DEVICE

INSPECTION DATA COMMUNICATION SYSTEM

COMMAND COMMUNICATION SYSTEM

INSPECTION DATA CONTROL SYSTEM
USING A REMOTE COMPUTING DEVICE

| SAMPLE | QUALITY CHARACTERISTIC | REQUIREMENT | PASS/FAIL? |
|---|---|---|---|
| 1 | NUMBER OF PITS | < 3 | PASS |
| 2 | NUMBER OF PITS | < 3 | PASS |
| 3 | NUMBER OF PITS | < 3 | FAIL |
| 4 | NUMBER OF PITS | < 3 | PASS |
| 5 | NUMBER OF PITS | < 3 | PASS |
| 6 | NUMBER OF PITS | < 3 | FAIL |
| 7 | NUMBER OF PITS | < 3 | PASS |
| 8 | NUMBER OF PITS | < 3 | PASS |
| 9 | NUMBER OF PITS | < 3 | FAIL |
| 10 | NUMBER OF PITS | < 3 | PASS |

*PASS PERCENTAGE = 70%*   *FAIL PERCENTAGE = 30%*
*NUMBER OF PASSING SAMPLES = 7*   *NUMBER OF FAILING SAMPLES = 3*

INSPECTION DATA

FIG. 18

| SAMPLE | QUALITY CHARACTERISTIC | REQUIREMENT | PASS/FAIL? |
|---|---|---|---|
| 1 | TYPE OF OBJECT | ALMOND | FAIL |
| 2 | TYPE OF OBJECT | ALMOND | PASS |
| 3 | TYPE OF OBJECT | ALMOND | FAIL |
| 4 | TYPE OF OBJECT | ALMOND | PASS |
| 5 | TYPE OF OBJECT | ALMOND | PASS |
| 6 | TYPE OF OBJECT | ALMOND | FAIL |
| 7 | TYPE OF OBJECT | ALMOND | PASS |
| 8 | TYPE OF OBJECT | ALMOND | PASS |
| 9 | TYPE OF OBJECT | ALMOND | FAIL |
| 10 | TYPE OF OBJECT | ALMOND | PASS |

*PASS PERCENTAGE = 60%*   *FAIL PERCENTAGE = 40%*
*NUMBER OF PASSING SAMPLES = 6*   *NUMBER OF FAILING SAMPLES = 4*

INSPECTION DATA

FIG. 19

| SAMPLE | QUALITY CHARACTERISTIC | REQUIREMENT | PASS/FAIL? |
|---|---|---|---|
| 1 | NUMBER OF HOLES | < 1 | PASS |
| 2 | NUMBER OF HOLES | < 1 | PASS |
| 3 | NUMBER OF HOLES | < 1 | FAIL |
| 4 | NUMBER OF HOLES | < 1 | PASS |
| 5 | NUMBER OF HOLES | < 1 | PASS |
| 6 | NUMBER OF HOLES | < 1 | FAIL |
| 7 | NUMBER OF HOLES | < 1 | PASS |
| 8 | NUMBER OF HOLES | < 1 | PASS |
| 9 | NUMBER OF HOLES | < 1 | FAIL |
| 10 | NUMBER OF HOLES | < 1 | PASS |

*PASS PERCENTAGE = 70%*      *FAIL PERCENTAGE = 30%*
*NUMBER OF PASSING SAMPLES = 7*      *NUMBER OF FAILING SAMPLES = 3*

INSPECTION DATA

FIG. 20

COMMAND BASED ON INSPECTION DATA

COMMAND BASED ON INSPECTION DATA

COMMAND BASED ON INSPECTION DATA

INSPECTION DATA COMMUNICATION SYSTEM FLOWCHART

COMMAND COMMUNICATION SYSTEM FLOWCHART

QUALITY INSPECTION DATA
DISTRIBUTED LEDGER FLOWCHART

| Data | |
|---|---|
| Inspection Entitiy | Food Source, Inc. |
| Inspection Location | Stockton, CA |
| Sensor Identification number | QIS-0112025 |
| Lot # | K00259-2683 |
| Total lot weight | 44,000 lbs |
| Analysis timestamp | 6/21/2018 8:17 |
| Amount of product analyzed | 1,000 gram |
| Moisture content | 4.55% |
| Kernel size | 24.38 |
| Uniformity ratio | 1.31 |
| Good | 87.50% |
| Dissimilar | 0.00% |
| Doubles | 1.50% |
| Chip & Scratch | 8.50% |
| Other Defects | 2.00% |
| Serious Damage | 0.50% |
| USDA grade | US Extra #1 |
| Hashes | |
| Present Block Hash | 0000000000000000000301fcfeb141088a93b77dc0d52571a1185b425256ae2fb |
| Previous Block Hash | 00000000000000000004b1ef0105dc1275b3adfd067aed63a43324929bed64fd7 |
| Next Block Hash | 0000000000000000000282ac9977c3d103a3c6bd873b1f7744e8d42b83239baa6 |
| Merkle Root | a89769d0487a29c73057e14d89a |

QUALITY INSPECTION DATA BLOCK IN A
QUALITY INSPECTION DISTRIBUTED LEDGER

FIG. 29

CONVEYOR FOR MANUAL INSPECTION OR SORTING

CONVEYOR WITH ADAPTABLE INSPECTION UNIT

CONVEYOR WITH ADAPTABLE SORTER UNIT

CONVEYOR WITH ADAPTABLE INSPECTION UNIT

CONVEYOR WITH ADAPTABLE SORTER UNIT

CONVEYOR WITH ADAPTABLE INSPECTION UNIT

CONVEYOR WITH ADAPTABLE SORTER UNIT

ALTERNATIVE ATTACHMENT MECHANISMS

CONVEYOR WITH ADAPTABLE INSPECTION UNIT AND ADAPTABLE SORTER UNIT

ADAPTABLE INSPECTION UNIT

ADAPTABLE SORTING UNIT

ADAPTABLE INSPECTION UNIT

ADAPTABLE SORTER UNIT

ADAPTABLE INSPECTION UNIT FOR EXISTING PROCESSING LINES

CROSS REFERENCE TO RELATED APPLICATIONS

This application is a continuation-in-part and claims priority under 35 U.S.C. 120 from nonprovisional U.S. patent application Ser. No. 16/031,956, entitled "QUALITY INSPECTION DATA DISTRIBUTED LEDGER", filed on Jul. 10, 2018, the subject matter of which is incorporated by reference. Application Ser. No. 16/031,956, is in turn a continuation-in-part and claims priority under 35 U.S.C. 120 from nonprovisional U.S. patent application Ser. No. 15/995,126, entitled "INSPECTION DEVICE CONTROLLED PROCESSING LINE SYSTEM", filed on Jun. 1, 2018, the subject matter of which is incorporated by reference. Application Ser. No. 15/995,126, in turn is a continuation and claims priority under 35 U.S.C. § 120 from nonprovisional U.S. patent application Ser. No. 15/817,240, entitled "INSPECTION DEVICE CONTROLLED PROCESSING LINE SYSTEM," filed on Nov. 19, 2017, the subject matter of which is incorporated herein by reference. Application Ser. No. 15/817,240, in turn, is a continuation-in-part and claims priority under 35 U.S.C. 120 from nonprovisional U.S. patent application Ser. No. 15/219,870, entitled "IN-FLIGHT 3D INSPECTOR", filed on Jul. 26, 2016, the subject matter of which is incorporated by reference.

TECHNICAL FIELD

The present invention generally relates to systems and methods for implementing an adaptable inspection unit for existing processing lines.

BACKGROUND INFORMATION

Processing lines are widely used to inspect and sort large quantities of a specific item. For example, processing lines are used to inspect and sort eatable items such as fruits and nuts. Alternatively, processing lines are used to inspect and sort pharmaceutical pills. A popular example of a simple processing line is a conveyor processing line where items are propelled through the processing line via a conveyor belt that is wound around the conveyor head pulley and tail pulley. Other examples of processing lines include, but are not limited to, a flume, a roller belt, a shaker (conventional and linear motion), a slide, a chute, a conveyor tube, a bucket elevator, and a screw conveyor.

To date, existing processing lines, such as conveyors, have not been adaptable to work with any improved processing devices.

SUMMARY

In a first novel aspect, an adaptable inspection unit includes an attachment mechanism, an inspection sensor device (optical receiver), a data port that is capable of transmitting information, and a power port that is connectable to a power source. The attachment mechanism, the inspection sensor device, the data port, and the power port are physically connected together.

In a second novel aspect, the adaptable inspection unit also includes a memory circuit and a processor circuit. The processing circuit controls the inspection sensor device and writes information transmitted via the data port.

In a third novel aspect, the attachment mechanism is a mounting bracket, a mounting bracket receptacle, a weldable material (metals or thermoplastics), a clamp, an adhesive, a magnet, a latch, a lock, a locating pin, a rail, a slide, locking pin, a bolt, a screw, gravity or friction. The attachment mechanism is used to connect the adaptable inspection unit to a processing line such that the adaptable inspection unit is capable of capturing an image of a sample traveling along the processing line.

In another novel aspect, the attachment mechanism affixes the adaptable inspection unit to a location proximate to a processing line such that the adaptable inspection unit is capable of capturing an image of a sample traveling along the processing line. In one example, the inspection is performed by an optical sensor, a moisture sensor, a microtoxin sensor, a thermometer sensor, an acidity sensor, a microwave sensor, a pressure sensor, a level sensor, an ultrasonic sensor, a flow sensor, a viscosity sensor, a conductance/impedance sensor, a electronic nose (sniffing) sensor, an X-ray sensor, a multi spectral (visual/non-visual) sensor, a weight sensor, a refractometer sensor, a tenderometer sensor, a firmness sensor, a hardness sensor, or a proximity sensor.

In yet another novel aspect, the adaptable inspection unit communicates with a sorting device via the data port. The data port can be either a wired communication port or a wireless communication port. To be clear, optical communications, such as fiber optics, are considered to be wired communications. Accordingly, the current description applies to data ports that communication via electrical signals traveling on metal wires, as well as optical signals traveling through optical conductors.

In another novel aspect, the adaptable inspection unit outputs sample characterization data via the data port. The information transmitted by the adaptable inspection via the data port unit causes a mode of operation of the sorting device to be performed.

In another novel aspect, an adaptable sorter unit includes an attachment mechanism, a sorting device that is capable of deflecting a sample, a data port that is capable of receiving information, and a power port that is connectable to a power source. The attachment mechanism, the sorting device, the data port, and the power port are physically connected together.

In another novel aspect, the adaptable sorter unit also includes a memory circuit and a processor circuit. The processor is configured to read information received via the data port and control the sorting device. The sorting device is a vacuum system, a mechanical pedal system, an air jet system, or a mechanical gate.

In another novel aspect, the attachment mechanism is a mounting bracket, a mounting bracket receptacle, a weldable material (metals or thermoplastics), a clamp, a bolt, or a screw.

In another novel aspect, the attachment mechanism connects the adaptable sorter unit to a processing line such that the adaptable sorter unit is capable of deflecting a sample traveling along the processing line. In one example, the sorting is performed by a vacuum system, a mechanical pedal system, an air jet system, or a mechanical gate.

In another novel aspect, the attachment mechanism affixes the adaptable sorter unit to a location proximate to a processing line such that the adaptable sorter unit is capable of deflecting a sample traveling along the processing line.

In another novel aspect, the adaptable sorter unit communicates with an optical inspection device via the data port. The data port is either a wired communication port or a wireless communication data port.

In another novel aspect, the adaptable inspection unit and/or the adaptable sorter unit is located proximate to a gap between two parts of a processing line. For example, proximate to the location where a sample travels from a chute portion of the processing line to a conveyor portion of the processing line. In this example, the adaptable inspection unit could be mounted so that it will inspect the sample while the sample travels between the chute portion of processing line and the conveyor portion of the processing line.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 18 is a diagram of a first example of inspection data.

FIG. 19 is a diagram of a second example of inspection data.

FIG. 20 is a diagram of a third example of inspection data.

FIG. 29 is a diagram of a quality inspection data block in a quality inspection distributed ledger.

DETAILED DESCRIPTION

Reference will now be made in detail to background examples and some embodiments of the invention, examples of which are illustrated in the accompanying drawings. In the description and claims below, relational terms such as "top", "down", "upper", "lower", "top", "bottom", "left" and "right" may be used to describe relative orientations between different parts of a structure being described, and it is to be understood that the overall structure being described can actually be oriented in any way in three-dimensional space.

Due to the drawbacks of human visual inspection, an automated inspector is needed to quickly, inexpensively and accurately detect defects present in objects such as tree nuts, tablets, screws and many other types of objects. Some of the most important features of such an automatic inspector include: cost, number of objects inspected per minute, accuracy of defect detection, reliability of defect detection and ease of use with minimal user training.

Figure 1:
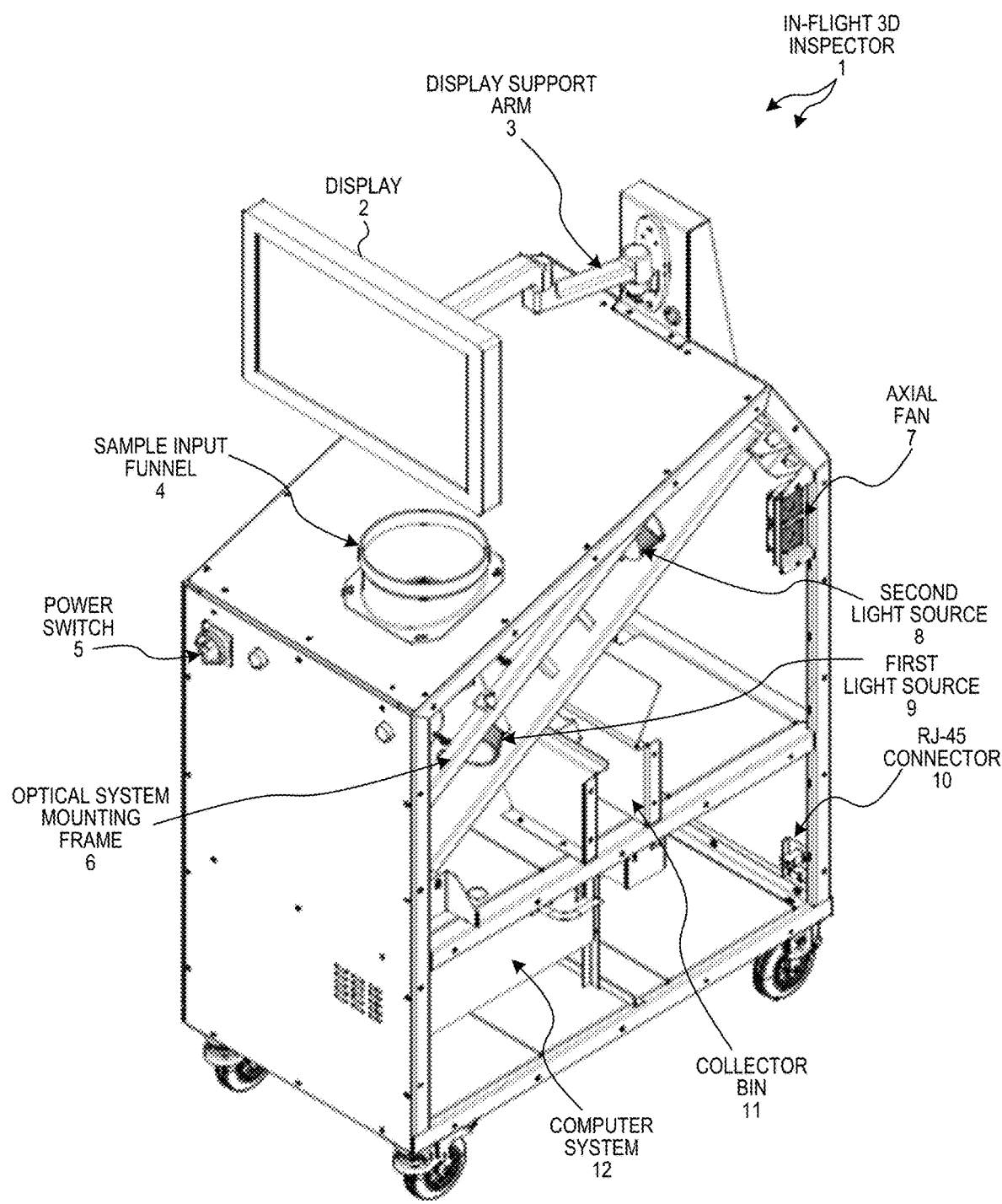
FIG. 1 is a first diagram of the in-flight 3D inspector 1 view from a first perspective.

FIG. 1 is a first diagram of the in-flight 3D inspector 1 view from a first perspective. The in-flight 3D inspector 1 includes a display 2, a display support arm 3, a sample input funnel 4, a power switch 5, an optical system mounting frame 6, an axial fan 7, a first light source 9, a second light source 8, an RJ-45 connector 10, a collector bin 11, and a computer system 12. The display 2 outputs information from the computer system 12 to a human user looking at the display. The display support arm 3 attaches the display 2 to the in-flight 3D inspector 1. In one example, the display support arm is adjustable with two hinges as shown in FIG. 1. In another example, the display support arm 3 is adjustable in additional dimensions (not shown in FIG. 1). The sample input funnel 4 is where samples are input to the in-flight 3D inspector. Power switch 5 is used by a human user to turn on (or off) the in-flight 3D inspector. The light sources are mounted to the optical system mounting frame 6. The axial fan 7 is used to create positive pressure in a camera enclosure (not shown in FIG. 1). In one example, the axial fan 7 is coupled to a first hose that directs air flow to a first camera enclosure and is coupled to a second hose that directs air flow to a second camera enclosure (not shown). The hoses can be fixed or flexible hoses made of various materials including various plastics, fiberglass and metal materials. In this fashion, positive pressure in each camera enclosure is created. The positive pressure prevents debris from entering the camera enclosures and settling on any of the cameras. RJ-45 connector 10 is configured to receive an RJ-45 cable connected to a local network and electrically connect the RJ-45 cable to a network input port included on the computer system 12. The RJ-45 cable may be an ethernet cable (not shown). Via the RJ-45 connector 10 and a RJ-45 ethernet cable, the computer system 12 can connect to a local network or the public internet. The computer system 12 may also include a wireless networking card (not shown) that allows computer system 12 to wirelessly communicate (i.e. WiFi or cellular connection) with a network without the need for a wired connection. The collector bin 11 is configured to collect samples that have completed their path through the in-flight 3D inspector.

Figure 2:
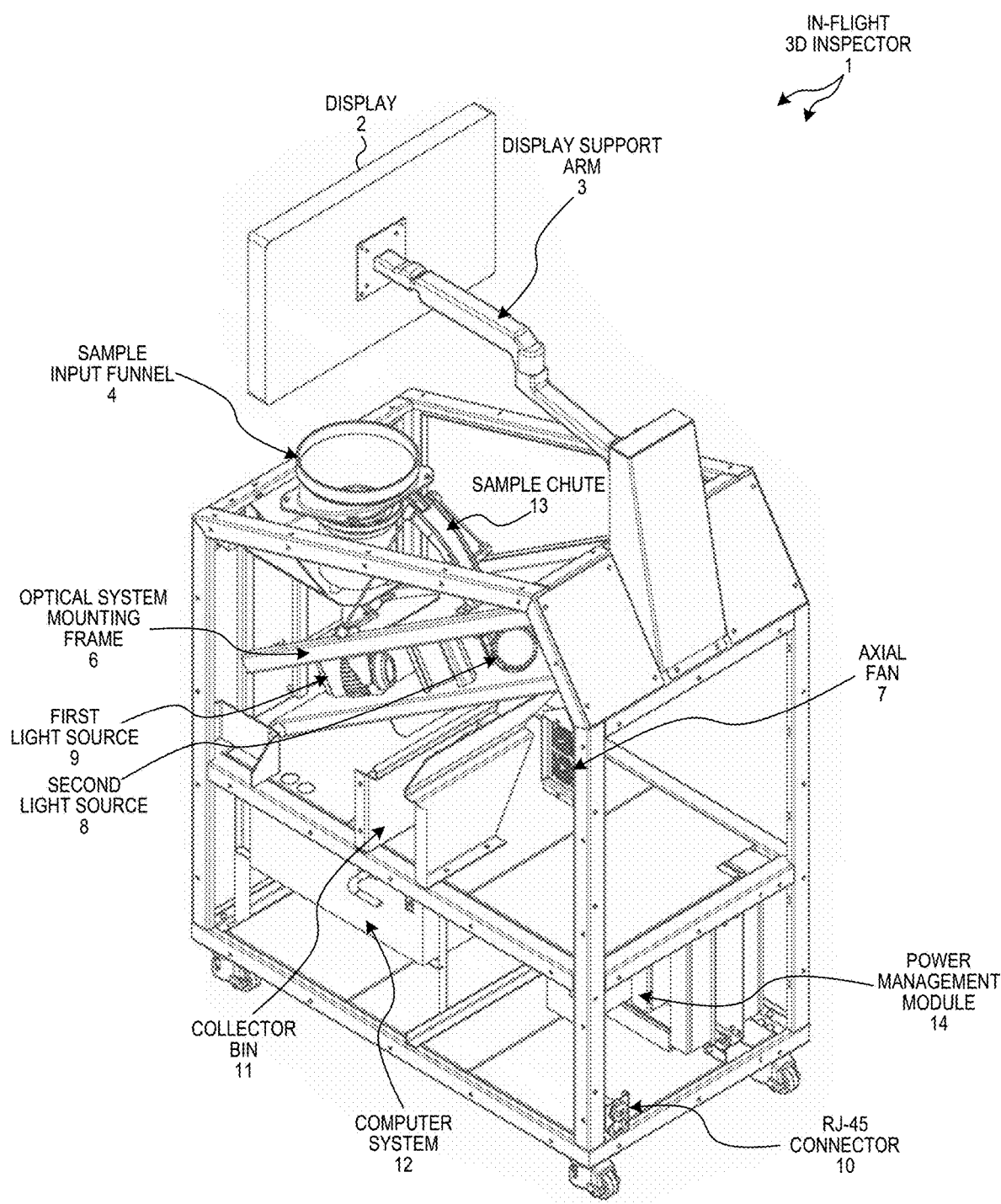
FIG. 2 is a second diagram of the in-flight 3D inspector 1 view from a second perspective.
Figure 14:
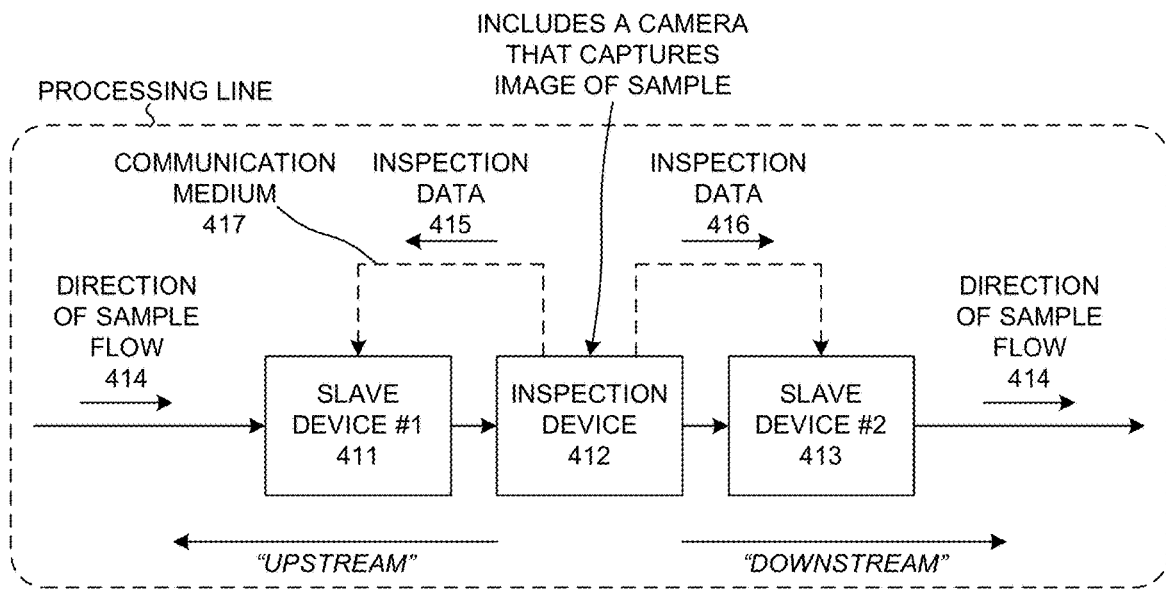
FIG. 14 is a diagram of an inspection data communication system.

FIG. 2 is a second diagram of the in-flight 3D inspector 1 view from a second perspective. FIG. 2 illustrates a sample chute 13 that is configured to guide a sample from the sample input funnel 4. The location of a power management module 14 is also shown in FIG. 14. The power management module 14 receives input power from the local power grid and generates power signals for the various electrical components operating within the in-flight 3D inspector 1. For example, the power management module 14 generates a power signal that is used to power the various light sources, the various cameras (not shown), the axial fan, the display and the computer system. In one example, the power management module 14 includes a battery which can be used to operate the in-flight 3D inspector when power from the local power grid is lost.

Figure 3:
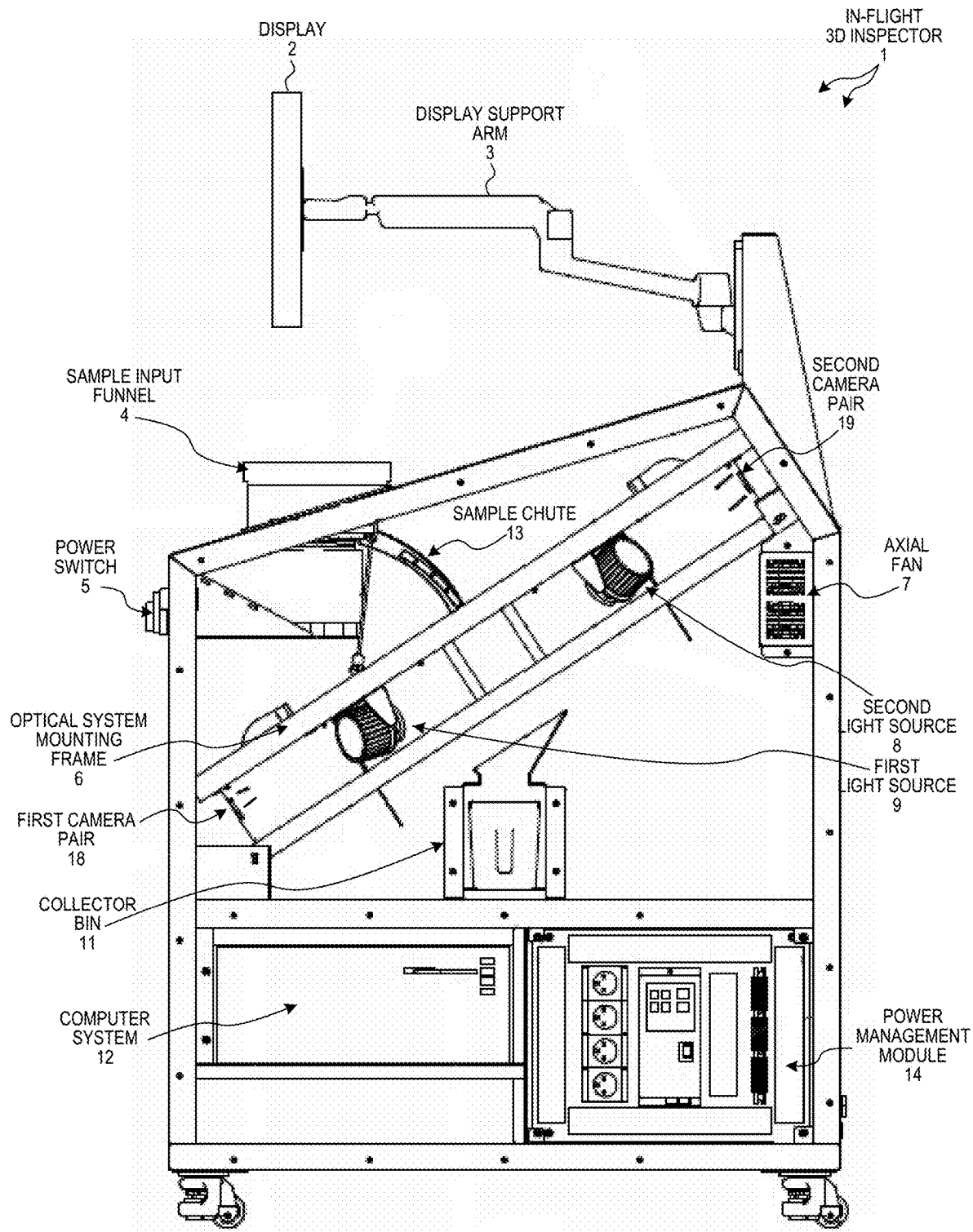
FIG. 3 is a third diagram of the in-flight 3D inspector 1 view from a right side view.
Figure 6:
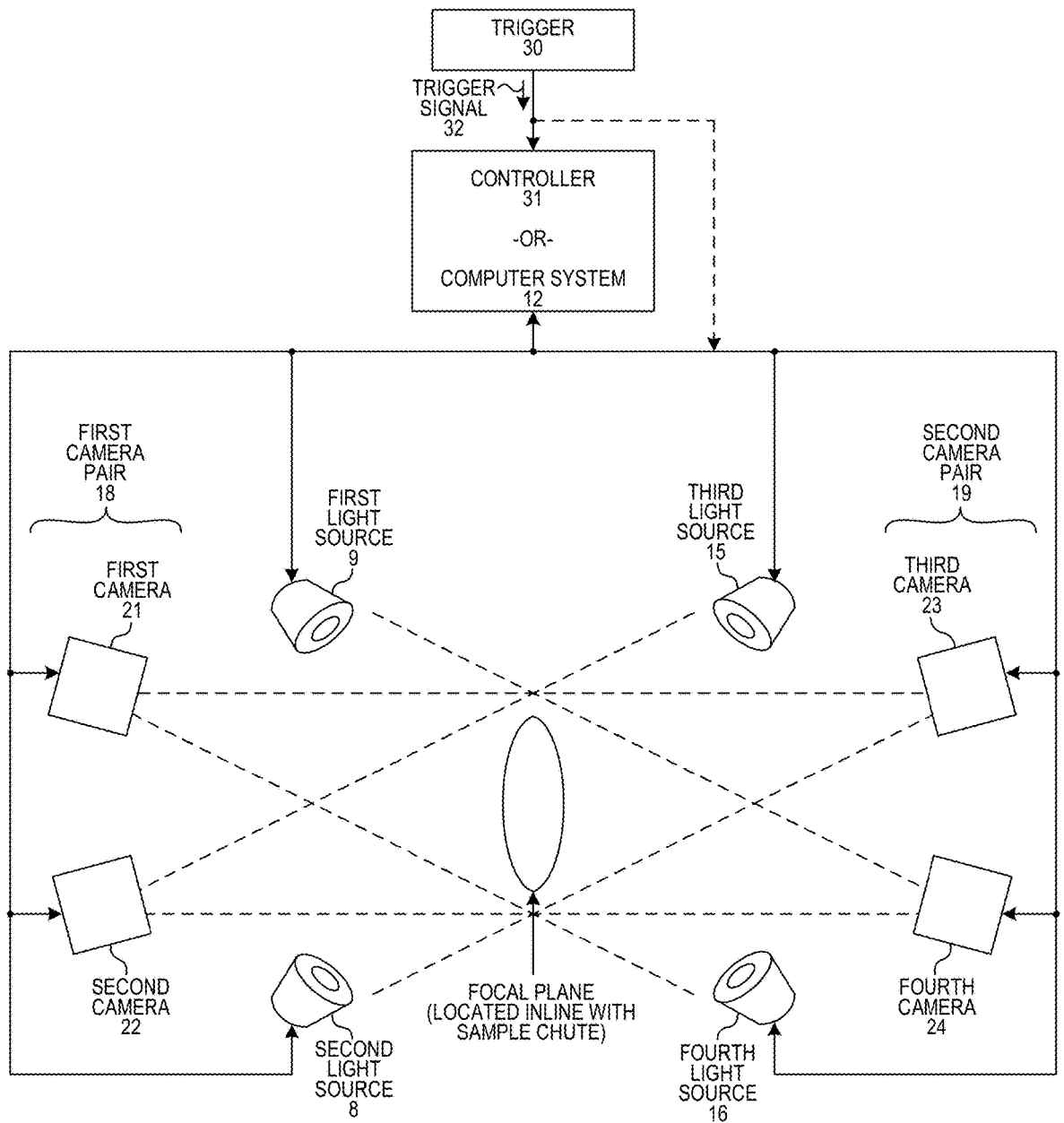
FIG. 6 is a diagram of a double stereo camera system configuration with triggering.

FIG. 3 is a third diagram of the in-flight 3D inspector 1 view from a right side view. FIG. 3 shows a first camera pair 18 and a second camera pair 19. FIG. 3 also illustrates that sample chute 13 is aligned with the midpoint between the first camera pair 18 and the second camera pair 19. The physical arrangement of the first camera pair 18 and the second camera pair 19 is illustrated in FIG. 6. FIG. 6 illustrates that the first camera pair 18 includes a first camera 21 and a second camera 22. The second camera pair 19 includes a third camera 23 and a fourth camera 24. All four cameras are focused on the same focal plane. The focal plane is located at the midpoint between the first camera pair 18 and the second camera pair 19. As discussed above regarding FIG. 3, the chute is also aligned with the midpoint between the first camera pair 18 and the second camera pair 19.

Camera Positioning

The four cameras are positioned such that each camera is focused on the focal plane. Each camera utilizes a lens to focus on the focal plane. In one example, wide angle lenses are used by each camera. One example of a wide angle lens is FL-BC1618-9M Ricoh lens. This wide angle lens has a format size of 1" format, a focal length of sixteen millimeters, a maximum aperture ratio of 1:1.8, an iris range of 1.8 to 16, and a resolution of nine mega-pixels. Other types of lenses may be used to achieve the necessary focus of each camera on the focal plane.

Figure 4:
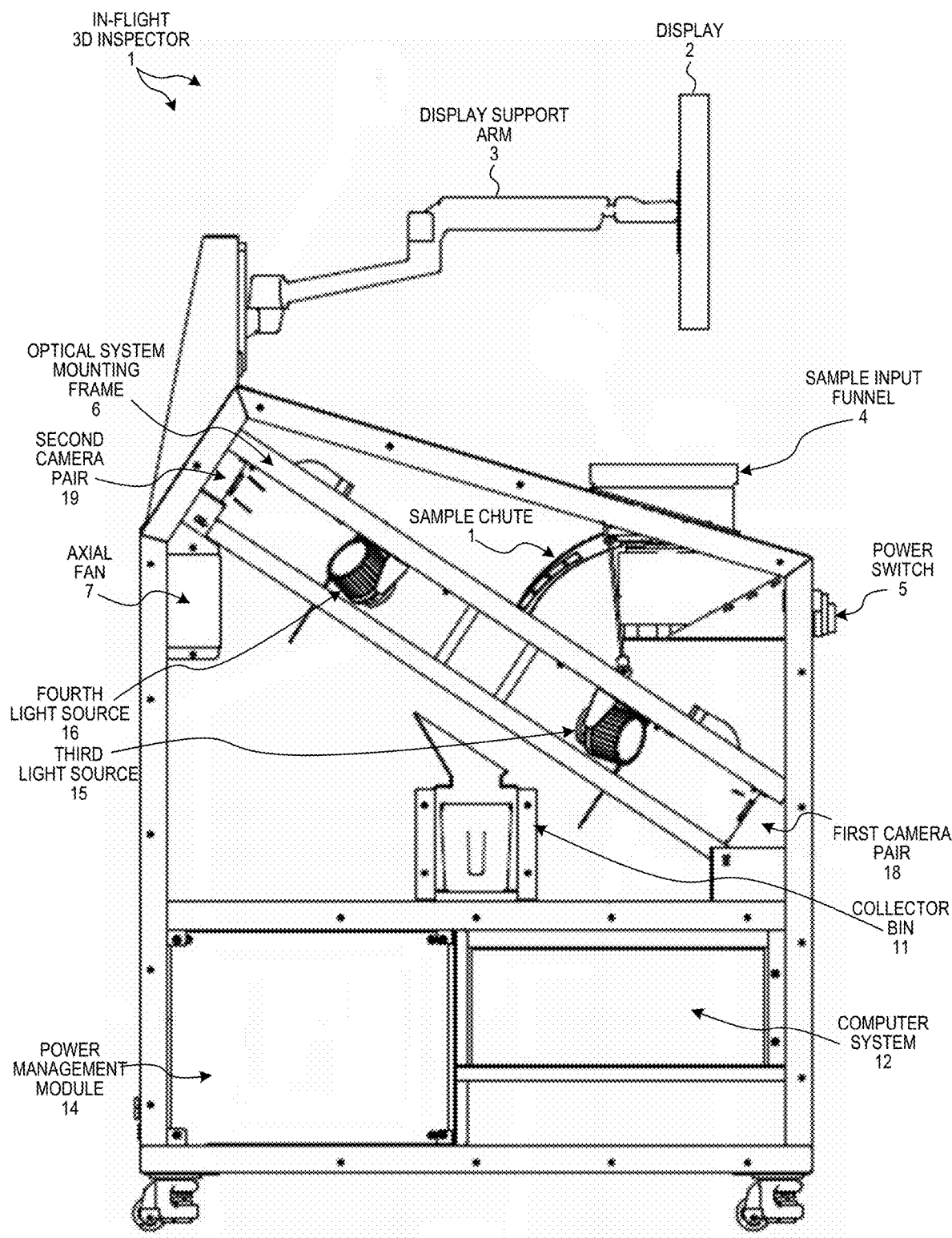
FIG. 4 is a fourth diagram of the in-flight 3D inspector 1 view from a left side view.

FIG. 4 is a fourth diagram of the in-flight 3D inspector 1 view from a left side view. FIG. 4 illustrates that a third light source 15 and a fourth light source 16 are also included in the in-flight 3D inspector 1. In one example, the first, second, third and fourth light sources are mounted to the optical system mounting frame 6. In another example, the light sources are mounted directly to outer frame of the in-flight 3D inspector 1 (not shown). After reading of the present disclosure, one skilled in the art will readily appreciate the various ways that light sources and cameras can be physically mounted within the in-flight 3D inspector 1.

Figure 5:
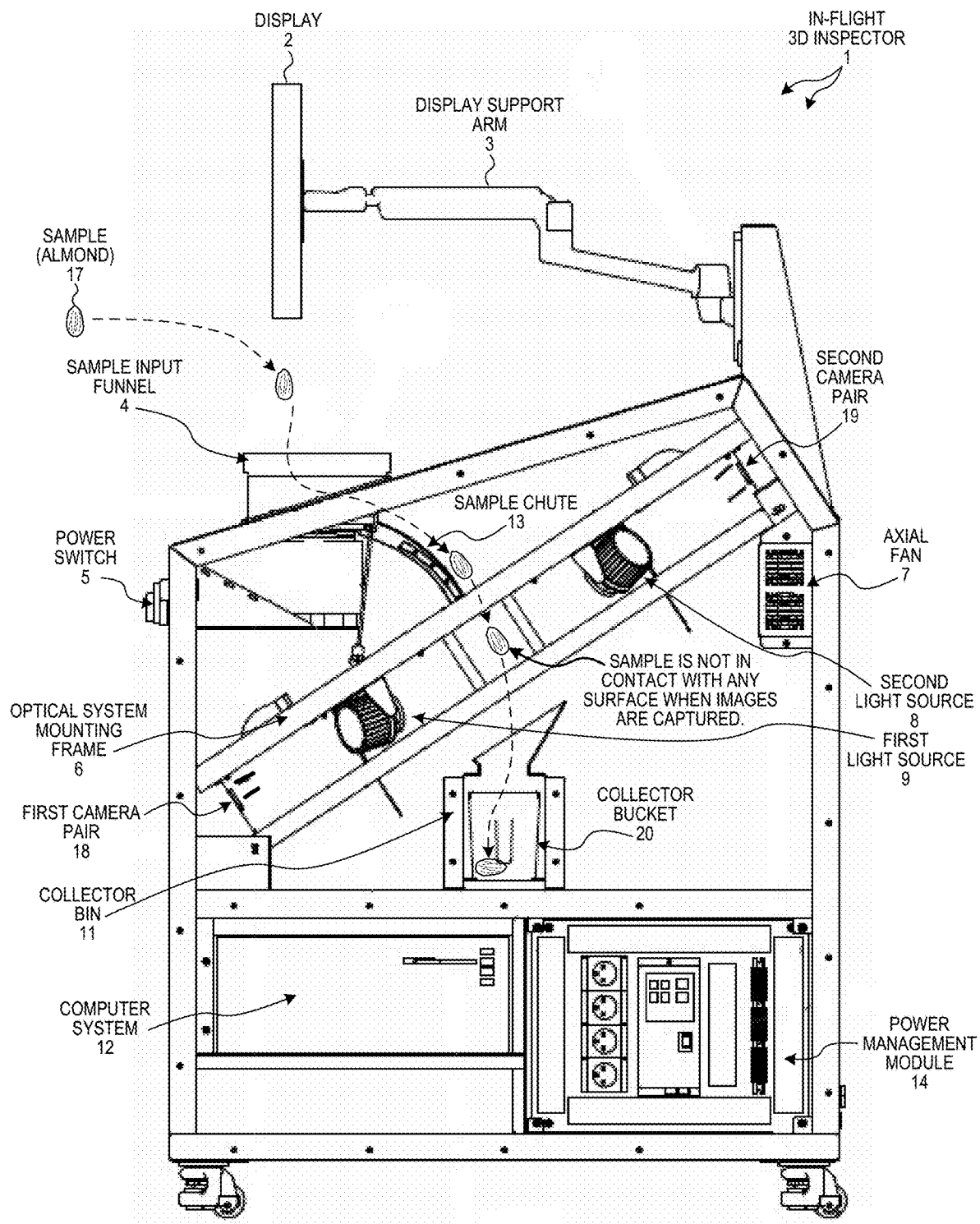
FIG. 5 is a diagram of the in-flight 3D inspector 1 illustrating the path a sample travels through the in-flight 3D inspector 1.

FIG. 5 is a diagram of the in-flight 3D inspector 1 illustrating the path a sample travels through the in-flight 3D inspector 1. First, a sample 17 is placed into the sample input funnel 4. The sample input funnel 4 directs the sample 17 to sample chute 13. In one example, the sample input funnel 4 is configured to vibrate such that sample 17 is directed toward sample chute 13. Sample chute 13 directs the sample 17 to a focal plane where the first camera pair 18 and the second camera pair 19 are both focused. In-flight 3D inspector 1 may be used to generate images of various types of samples, such as tree nuts, a peanuts, tablets, screws and washers.

Triggering System

Before the sample 17 reaches the focal plane, a trigger senses the presence of the sample 17 near the sample chute 13 and generates a trigger signal. In one example, the trigger is attached to the sample chute 13 and includes an optical transmitter and an optical receiver. In operation, the sample 17 interferes with the light traveling between the optical transmitter and the optical receiver as sample 17 travels along sample chute 13. This interference in received light is sensed by the optical receiver when the transmitted light does not irradiate the optical receiver. In response to detecting the interference in received light, the trigger generates a trigger signal. The trigger signal can be an electric signal that propagates along a conductor, or the trigger signal can be an electro-magnetic signal that propagates across free space to a receiving terminal. The duration between the time when the trigger signal is generated and the time when the sample 17 intersects the focal plane is based on where the trigger is located relative to the focal plane of the camera pairs. Once the trigger location is selected the duration between the time when the trigger signal is generated and the time when the sample 17 intersects the focal plane can be empirically measured or calculated. Once the duration between when the trigger signal is generated and the time when the sample 17 intersects the focal plane has been determined, the trigger signal can be used to determine the future time when the sample 17 will intersect the focal plane. This timing information can be used to properly control the various light sources and cameras in the in-flight 3D inspector.

The trigger is not shown in FIG. 5. However, a system diagram of the triggering system is illustrated in FIG. 6. FIG. 6 is a diagram of a double stereo camera system configuration with triggering. The triggering system includes trigger 30, controller 31 and/or computer system 12, cameras 21-24 and light sources 8-9 and 15-16. In one example, the trigger signal 32 (i) causes light sources 8, 9, 15, and 16 to turn on, and (ii) causes the first camera pair 18 and the camera pair 19 to capture an image when the sample 17 intersects in the focal plane. In another example, light sources 8, 9, 15 and 16 are already on and the trigger signal 32 only causes the first camera pair 18 and the camera pair 19 to capture an image when the sample 17 intersects in the focal plane.

In a first embodiment, the trigger signal is communicated from the trigger 30 to a controller 31 that controls when the first camera pair 18 and the second camera pair 19 capture images. In a second embodiment, the trigger signal 32 is communicated from the trigger 30 directly to the first camera pair 18 and the second camera pair 19 and causes the camera pairs 18 and 19 to capture images. In a third embodiment, the trigger signal 32 is communicated from the trigger 30 to computer system 12 that controls when the first camera pair 18 and the second camera pair 19 capture images.

In a fourth embodiment, the trigger signal is communicated from the trigger 30 to a controller 31 that controls when the light sources 8-9 and 15-16 are turned on. The controller 31 acts as a switch that connects an output power terminal of a power supply included in power management module 14 to a power input terminal of each light source 8-9 and 15-16. The controller switch turns ON the light sources in response to receiving the trigger signal. After the sample has passed though the focal plane, the controller turns OFF the light sources by disconnecting the output power terminal of the power supply from the power input terminal of each light source.

In a fifth embodiment, the trigger signal 32 is communicated from the trigger 30 directly to the light sources 8-9 and 15-16 and causes the light sources 8-9 and 15-16 to turn ON. In this embodiment, each light source 8-9 and 15-16 is configured to receive a power signal and an ON/OFF signal. The ON/OFF signal is controlled by the trigger signal. The light sources may include a timer circuit that is used to turn OFF the light sources after the sample has passed through the focal plane.

In a sixth embodiment, the trigger signal 32 is communicated from the trigger 30 to computer system 12 that controls when the light sources 8-9 and 15-16 are turn on. In this embodiment, each light source 8-9 and 15-16 is configured to receive a power signal and an ON/OFF signal. The ON/OFF signal is output by the computer system 12 in response to receiving the trigger signal from the trigger.

The light sources may be controlled such that the light sources turn on after the camera shutters are opened and turn off before the camera shutters are closed.

Controller 31 may be configured to communicate with computer system 12 via an RS232 communication link, an ethernet communication link, an Universal Serial Bus (USB) communication link, or any other available data communication links.

Figure 7:
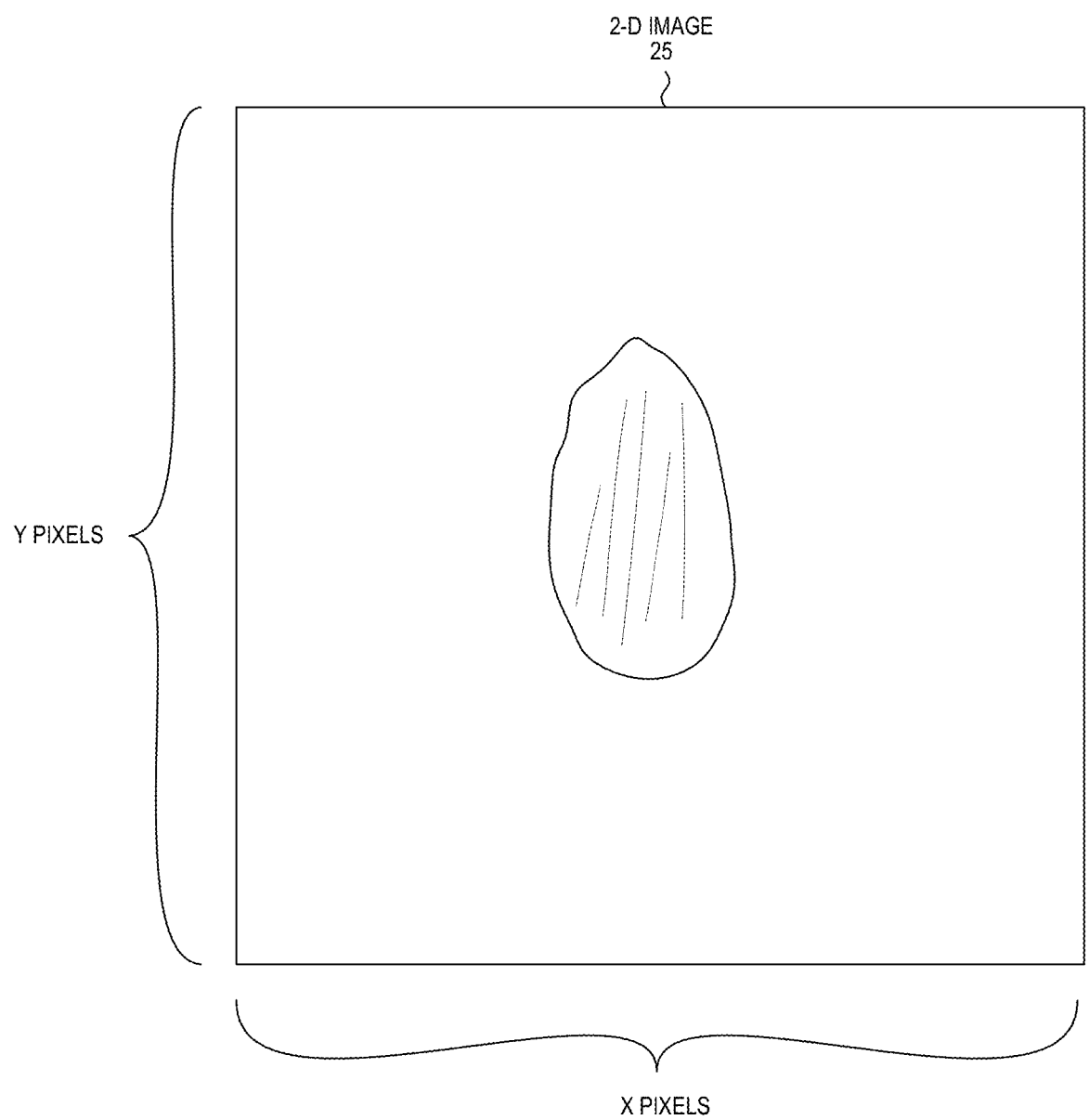
FIG. 7 is an image captured by a first camera of the double stereo camera system.
Figure 8:
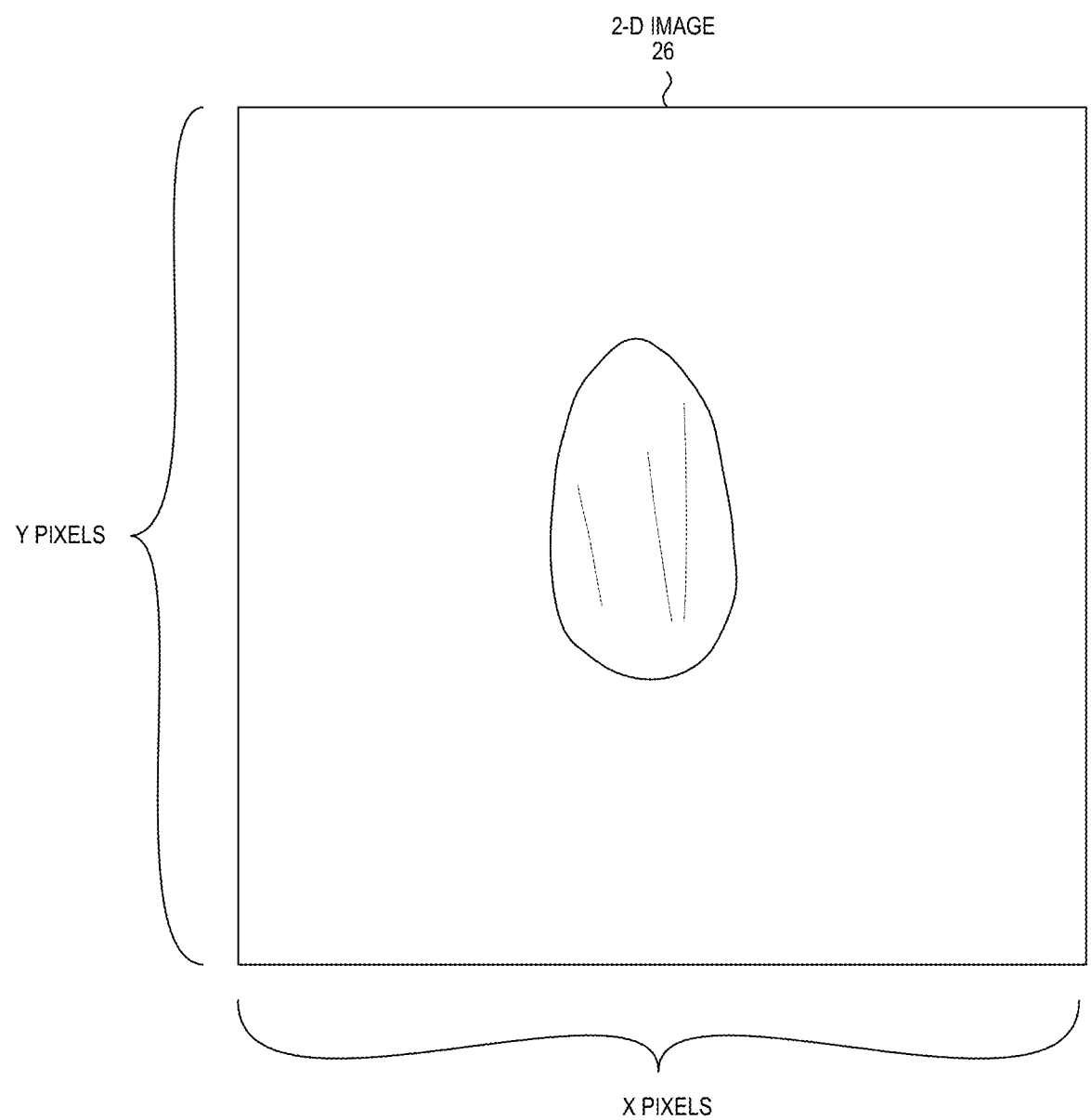
FIG. 8 is an image captured by a second camera of the double stereo camera system.
Figure 9:
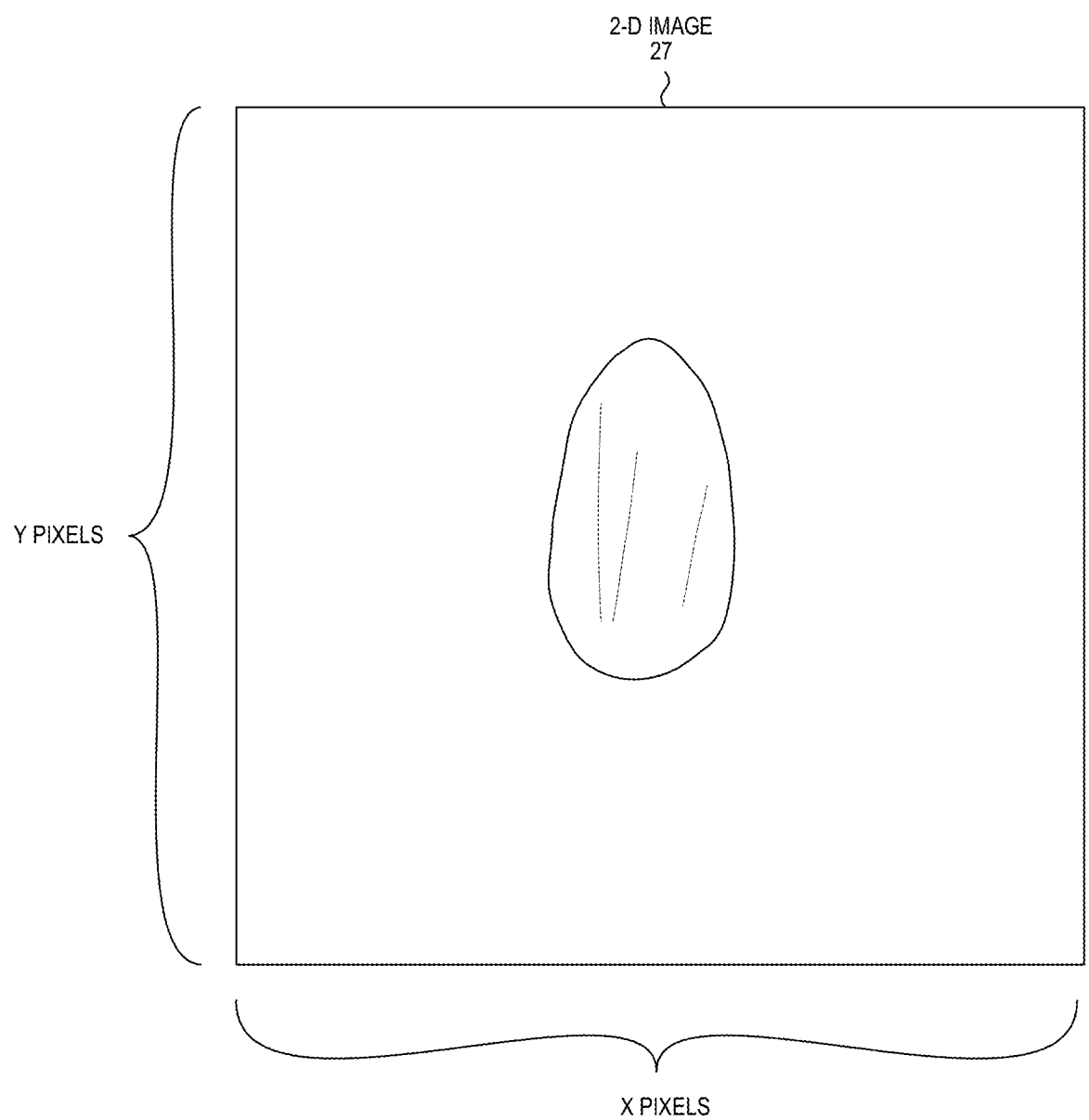
FIG. 9 is an image captured by a third camera of the double stereo camera system.
Figure 10:
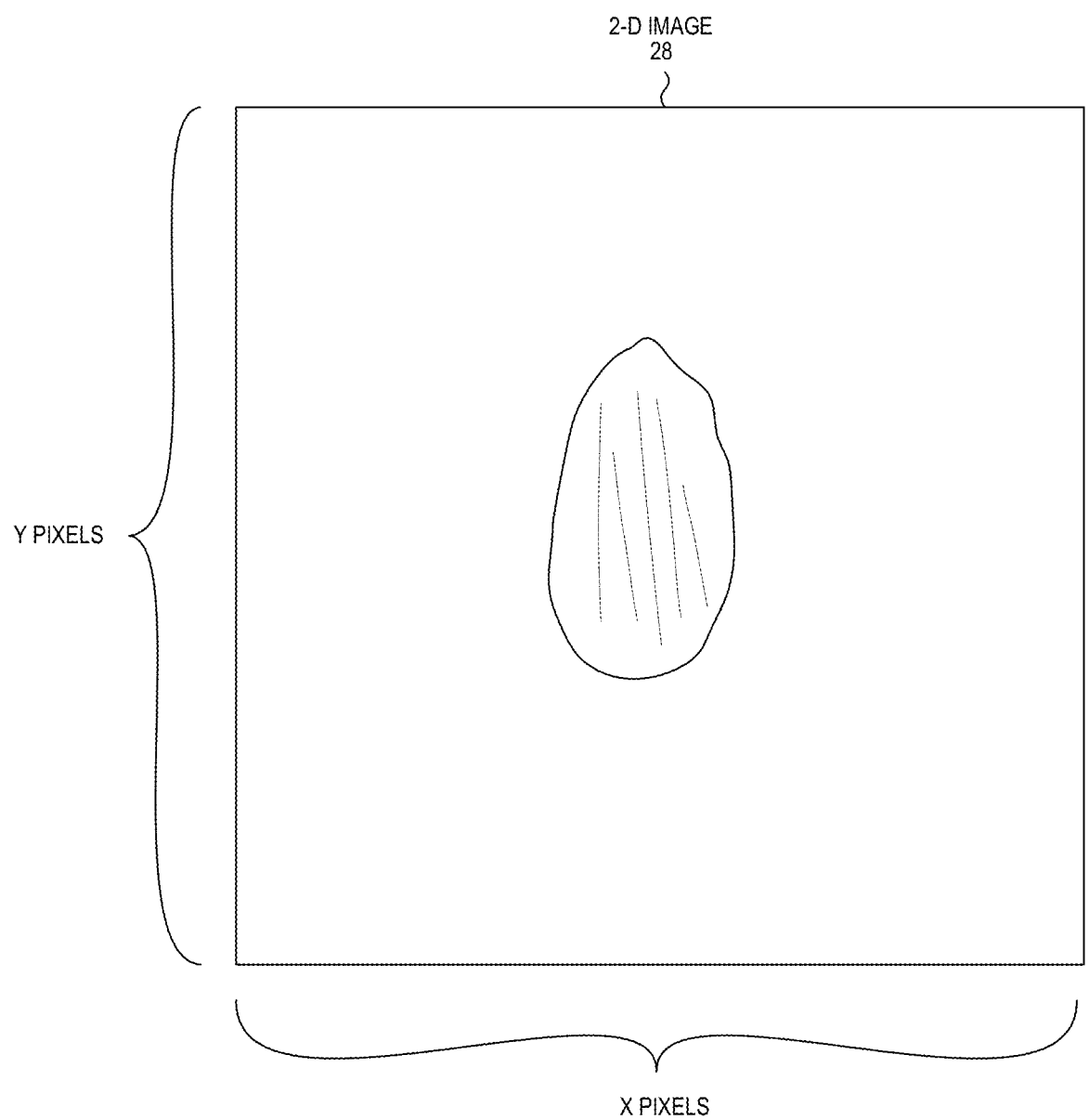
FIG. 10 is an image captured by a fourth camera of the double stereo camera system.

When the sample 17 travels through the focal plane, sample 17 is not contacting any surface. At this point in time, the light sources 8-9 and 15-16 are turned on and the first camera pair 18 and the second camera pair 19 capture at least one image of the sample. Each camera captures an image from a unique angle at the same moment in time as the sample travels through the focal plane. FIG. 7 is an image captured by a first camera of the double stereo camera system. FIG. 8 is an image captured by a second camera of the double stereo camera system. FIG. 9 is an image captured by a third camera of the double stereo camera system. FIG. 10 is an image captured by a fourth camera of the double stereo camera system. Each of these images is stored on a memory device located on the in-flight 3D inspector. On one example, the memory device is located within the computer system 12. It is noted that the captured images may only be temporarily stored on a memory device within the in-flight 3D inspector before being communicated across a network to another storage device located outside of the in-flight 3D inspector. For example, the captured images stored on a storage device within the computer system 12 may be communicated across RJ-45 connector 10 and a local network to another storage device not included in the in-flight 3D inspector. In this fashion, multiple images of the sample 17 are captured from four different angles at the same moment while the sample 17 is traveling through the focal plane while not in contact with any surface.

Capturing of images while the sample is not contacting any surface provides a great benefit. When the sample is not contacting any surface, images of each surface of the sample can be collected at the same moment in time. This is not possible in other image capturing systems. For example, when a sample is moved along a conveyer belt image of only one side of the sample may be captured at any one moment in time. View of the other side of the sample is blocked by the conveyer belt and therefore cannot be captured at the same moment in time. Capturing images of all surfaces of the sample at the same moment in time allows for generation of high quality 3D images of the sample. When images of various surfaces of the sample are taken at different moments in time, proper alignment of images is very difficult, requires additional processing and result in 3D images with lower quality due to introduced error.

The cameras communicate the captured images to the controller 31 or computer system 12 via bus. In one example, the bus is an Universal Serial Bus (USB). In another example, the bus is an IEEE 1394 "FireWire" bus.

In one example, the cameras (also referred to herein as a "image capturing device" or "optical receiver") are Charged Coupled Device (CCD) cameras. In another example, the cameras (also referred to herein as a "image capturing device" or "optical receiver") are Complementary Metal-Oxide Semiconductor (CMOS) cameras. In yet another example, the cameras (also referred to herein as a "image capturing device" or "optical receiver") are Indium Gallium Arsenide (InGaAs) cameras that are capable of measuring Short Wave Infra Red (SWIR) light.

Either line scan cameras and area scan cameras can be used to implement an in-flight 3D inspector. A line scan cameras contain a single row of pixels used to capture data very quickly. As the object moves past the camera, a complete image can be reconstructed in software line by line. Area scan cameras contain a matrix of pixels that capture an image of a given scene. They are more general purpose than line scan cameras, and offer easier setup and alignment.

It is noted herein that the light sources may each include a separate power source that drives the light when a control signal is received. Alternatively, each light source may be configured in an always on state where the power input terminal on each light source is coupled to an output terminal of a power supply where the output of the power supply is controlled by a control signal.

It is noted that the sample chute 13 is only one example how the sample can be directed to the focal plane. In a first alternative embodiment, the sample can be directed to the focal plane by use of a conveyer belt. In this first alternative embodiment, the sample would be directed from the sample input funnel to the conveyer belt, which in turn would propel the sample off the edge of the conveyer belt toward the focal plane. In a second alternative embodiment, the sample can be directed to the focal plane by use of an airburst. In this second alternative embodiment, the sample would be directed proximate to an airburst source, which in turn would propel the sample toward the focal plane. One example of an airburst source is a highly pressurized air tank connected to an electronically controlled valve, which outputs an airburst momentarily while the valve is open.

Sample Collection/Sorting

Once the sample 17 passes the focal plane, the sample 17 falls into collector bin 11. In one example, a collector bucket 20 is placed in collector bin 11. In this example, the sample 17 falls into the collector bucket 20. Additional samples placed into sample input funnel 4 make their way through the in-flight 3D inspector and eventually also fall into collector bucket 20. Once all samples have passed through the in-flight 3D inspector, a user can remove all samples by removing the collector bucket 20 from the collector bin 11.

In another example, a collector bucket 20 is not placed in collector bin 11. Rather, collector bin 11 is coupled to a sample sorting machine (not shown). In this example, the samples that pass through the in-flight 3D inspector are routed into different bins. The bin each sample is routed into is based on the images captured of the sample. In the event that the images of the sample indicate that the sample has a first type of defect, then the sample is routed to a first bin. In the event that the images of the sample indicate that the sample has a second type of defect, then the sample is routed into a second bin. Alternatively, in the event that the images of the sample indicate that the sample does not have any defects, then the sample is routed to a third bin. The sorting machine can route the samples using various different methods. A first method of routing includes using a burst of air to redirect the trajectory of a sample as it falls into the collector bin. A second method of routing includes using a mechanically controlled flap to redirect the trajectory of a sample as it falls into the collector bin.

3D Image Generation

Once the images are captured from each of the cameras, a 3D image of the sample can be created. In one example, the 3D image is generated by the computer system 12 included in the in-flight 3D inspector. In another example, the 3D image is generated by another computer system not included in the in-flight 3D inspector after the images are communicated across a network from the in-flight 3D inspector to the computer system not included in the in-flight 3D inspector.

The images captured by the first camera pair 18 are used to create a 3D image of a first side of the sample. The images captured by the second camera pair 19 are used to create a 3D image of the second side of the sample. In one example, data included in the captured 2D images are combined into a new dataset and missing information is added to complete the 3D information of the object: depth (distance). By using triangulation on matching pixels of the multiple 2D images captured by the in-flight 3D inspector, the depth component is derived and added to the dataset. This new dataset describes the object in 3D. This dataset is then used by advanced mathematical algorithms to describe the characteristics of the objects. The 3D images of the first and second sides of the sample are combined to create a 3D image of the entire sample. Once the 3D image of the entire sample is constructed, the 3D image can be analyzed to determine if various types of defects are present on the sample. For example, if the 3D image does not match a predetermined shape within a specified tolerance, then the sample is determined to be defective with respect to shape. In another example, if the 3D image shows a flat surface greater than a specified area, then the sample is determined to be defective with respect to surface contour.

Once the defect information is determined based on the 3D image of the sample, the defect information is stored with the 3D image. The defect information can be displayed on display 2 to a user of the in-flight 3D inspector. The defect information can also be used to generate a report indicating the number of defects detected across a multiple samples that have been inspected. The defect information for each sample can be used by a sorting machine attached to the collector bin 11 of the in-flight 3D inspector to determine how the sample is to be routed. The defect information for multiple samples can be used to generate a quality report indicating the quality grade of the multiple samples.

Various calibrations of the cameras may be performed. An internal calibration may be performed for each camera. Internal calibration includes calibration of principle points, focal lengths, pixel size ratios, and radial parameters. A stereo calibration may be performed as well. A stereo calibration addresses the external 3D rotation and translation between individual cameras of a stereo system. An inter-stereo calibration may also be performed to address the external 3D rotation and translation between the two stereo systems. In an inter-stereo calibration, a transformation is performed that stitches two different side reconstructions into one 3D model.

Capturing Images of Multiple Samples in a Single Image

The single sample chute 13 illustrated in FIG. 5 illustrates one embodiment of the present invention. In another embodiment (not shown in FIG. 5) the sample chute may be configured to direct multiple samples through the focal plane at the same moment in time. In this embodiment, the sample chute would cause multiple samples to fall through the focal plane along a single axis at the same time. Aligning the samples along a single axis prevents one sample from blocking a camera's view of another sample. The first and second camera pairs would then capture an image including multiple samples instead of just one. Said another way, a single image would include multiple samples instead of just one. Once the images of the multiple samples are captured, the computer system 12 would (i) determine which portions of each image are of each sample, and (ii) only use the portions of each image that are of the same sample to generate the 3D image of the sample.

This configuration would greatly accelerate the rate at which the in-flight 3D inspector can capture images of multiple samples. For example, if the sample chute directed ten samples through the focal plane as the same time instead of only one sample, then the in-flight 3D inspector would be able to collect images of samples ten times faster. Said another way, the in-flight 3D inspector would only require one-tenth the amount of time to collect images of a set of samples.

Figure 11:
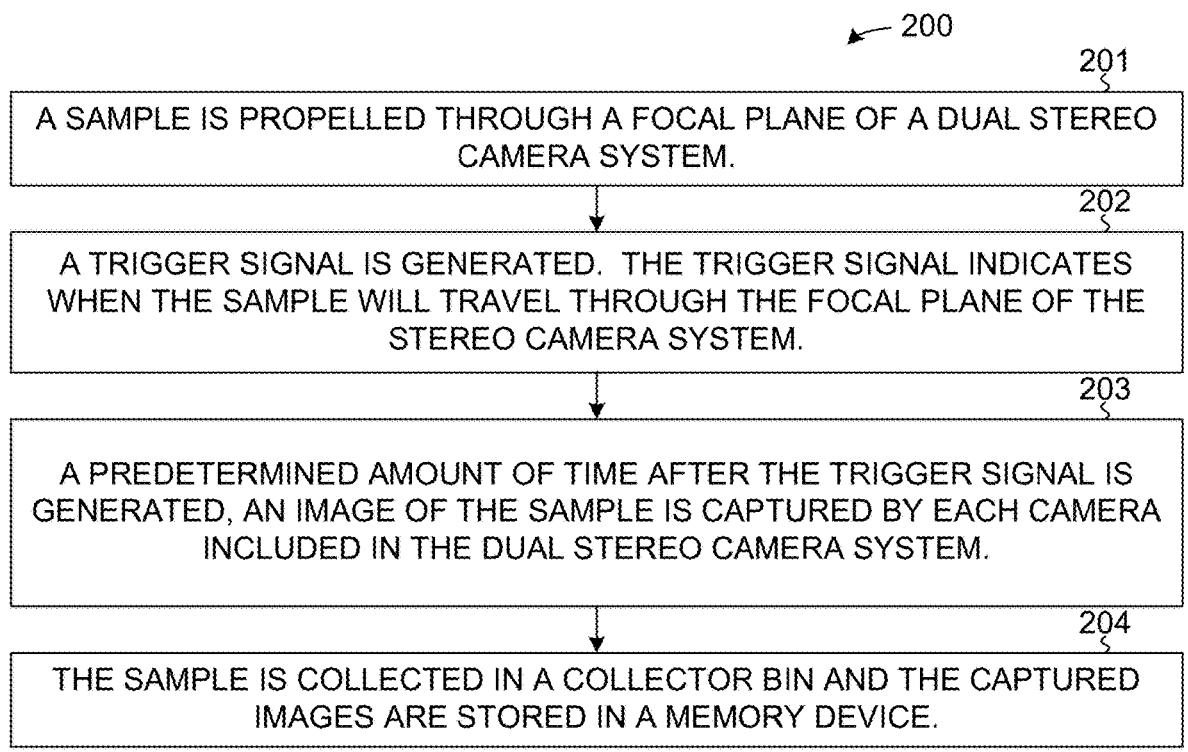
FIG. 11 is a flowchart of an in-flight 3D inspector.

FIG. 11 is a flowchart 200 of an in-flight 3D inspector. In step 201, a sample is propelled through a focal plane of a dual stereo camera system. In step 202, a trigger signal is generated. The trigger signal indicates when the sample will travel through the focal plane of the stereo camera system. In step 203, a predetermined amount of time after the trigger signal is generated, an image of the sample is captured by each camera included in the dual stereo camera system. The sample is illuminated by a light source while the image of the sample is captured. In step 204, the sample is collected in a collector bin and the captured images are stored in a memory device.

Figure 12:
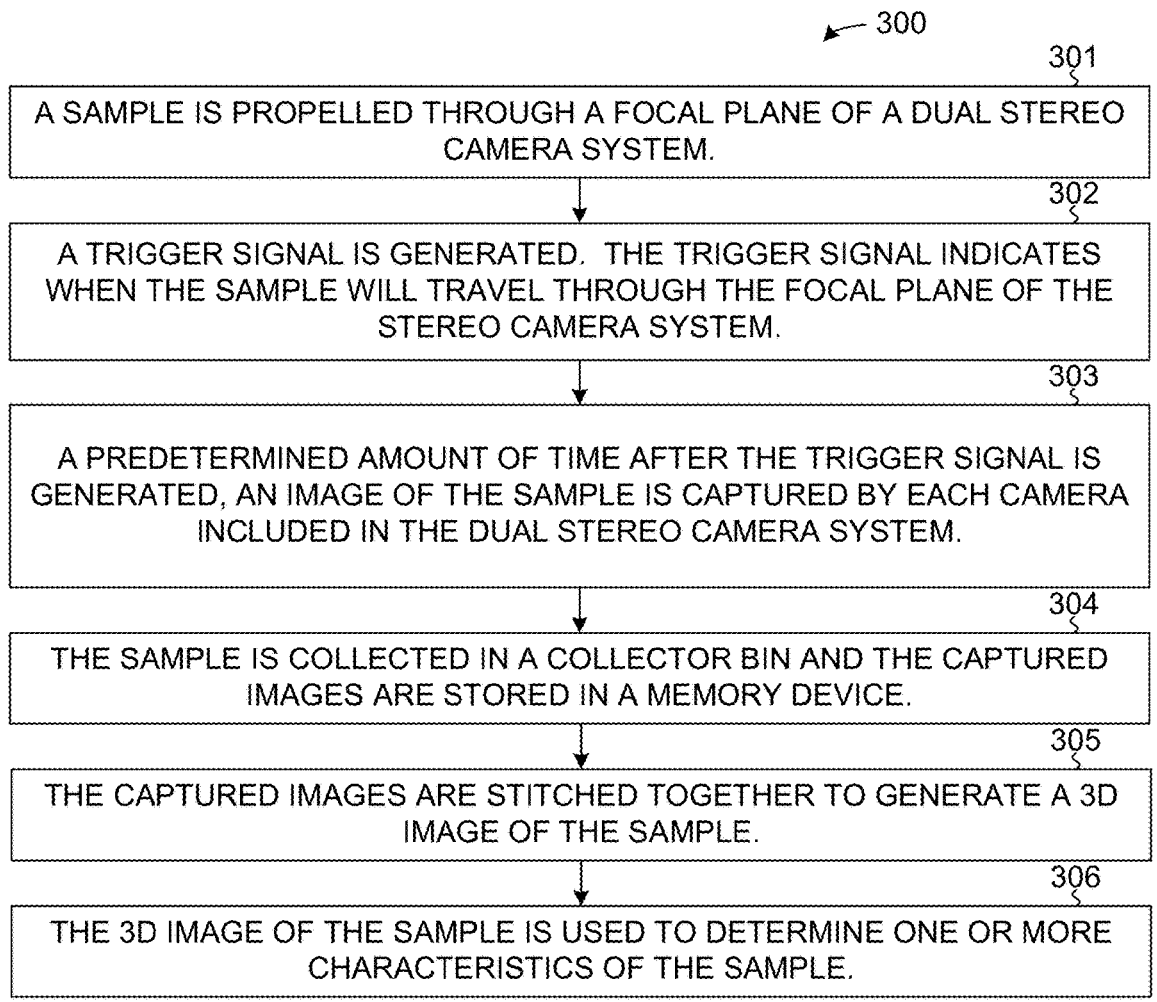
FIG. 12 is a flowchart of an in-flight 3D inspector with defect processing.

FIG. 12 is a flowchart 300 of an in-flight 3D inspector with defect processing. In step 301, a sample is propelled through a focal plane of a dual stereo camera system. In step 302, a trigger signal is generated. The trigger signal indicates when the sample will travel through the focal plane of the stereo camera system. In step 303, a predetermined amount of time after the trigger signal is generated, an image of the sample is captured by each camera included in the dual stereo camera system. The sample is illuminated by a light source while the image of the sample is captured. In step 304, the sample is collected in a collector bin and the captured images are stored in a memory device. In step 305, the captured images are stitched together to generate a 3D image of the sample. In step 306, the 3D image of the sample is used to determine one or more characteristics of the sample.

Various Numbers of Cameras can be Used

The two pairs of cameras 18-19 discussed above are used in a first embodiment of the present invention. In other embodiments, various other numbers of cameras may be used. For example, in another embodiment, the in-flight 3D inspector may include only one pair of stereo cameras that capture two images of the sample and the images are used to construct a 3D image of the sample from only one point of view. In another embodiment, three pairs of stereo cameras can be used to capture six images of the sample and the images are used to construct a 3D image of the sample from three points of view. After review of this disclosure, the reader will appreciate that additional cameras will provide additional accuracy of the 3D image created by the in-flight 3D inspector.

Inspection Device Controlled Processing Line System

Figure 13:
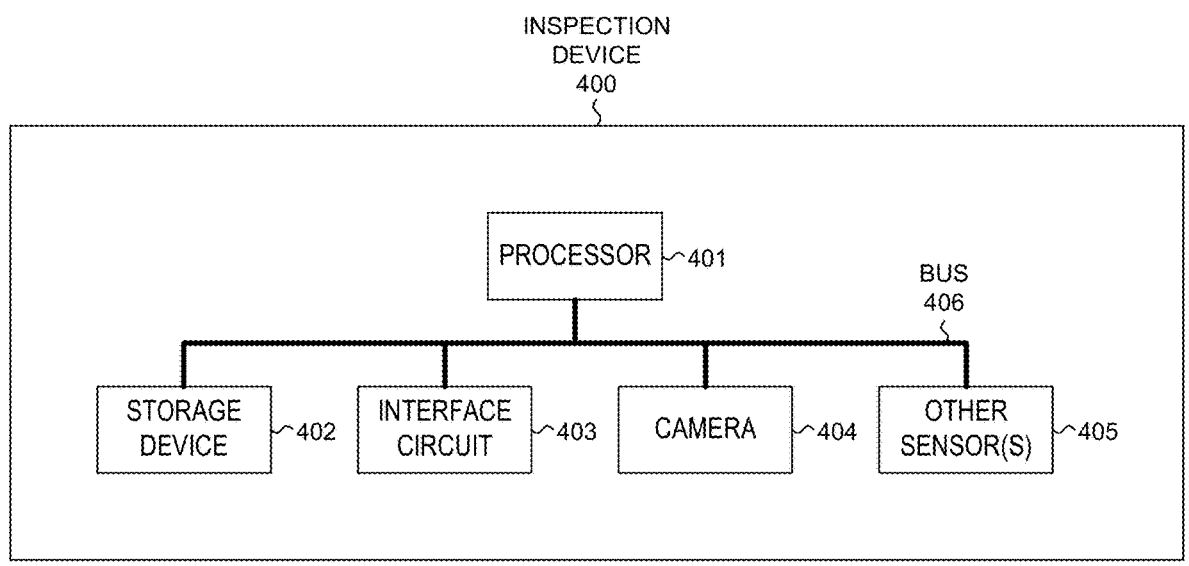
FIG. 13 is a diagram of an inspection device.

FIG. 13 is a diagram of an inspection device 400. Inspection device 400 includes a processor 401, a storage device 402, an interface circuit 403, an optical device 404 and/or other sensors 405. The various parts of inspection device 400 communicate with each other across a bus 406. On skilled in the art will note that various known bus architectures can be used to implement inspection device 400. One example of a bus architecture is Peripheral Component Interconnect Express (PCIe), which provides standardized communication between various device components. However, many other possible options exist, such as: Ethernet for Control Automation Technology (EtherCAT), Ethernet Industrial Protocol (EtherNet/IP), Process Field Net (PROFINET), Ethernet Powerlink, Third Generation of the Sercos Interface (SERCOS III), Control and Communication Link (CC-Link IE), and Modbus/TCP, Modbus, Sinec H1, Process Field Bus (Profibus), Controller Area Network Protocol (CANopen), DeviceNet, and FOUNDATION Fieldbus. One example of a processor is an intel x86 processor. One example of a storage device is a NAND flash based solid state drive. One example of an interface circuit is a Network Interface Card (NIC) that communicates across a physically connected cable to a network switch or router. Another example of an interface circuit is a Wireless Network Interface Controller (WNIC) that communicates across standards such as WiFi (802.11 protocols), Bluetooth and other such protocols. Another example of an interface circuit is a cellular communication device that communicates across cellular networks that use protocols such as GSM, WCDMA, CDMA2000, LTE, etc. All of the above mentioned communication methods may be used to implement a data port. An example of an optical device is a high shutter speed, high resolution digital camera that is controllable by a computer across a standardized data port, such as USB. Other examples of optical devices include, but are not limited to, millimeter wave cameras, Near-Infr-Red (NIR) cameras, hyper-spectral cameras, and x-ray cameras. Other sensors 405 may include audio, electromagnetic, and odor sensors that are controllable by a computer across a standardized bus, such as USB. Other examples of sensors include, but are not limited to weight scale sensors, proximity sensors, temperature sensors, humidity sensors, texture sensors, and moisture sensors.

FIG. 14 illustrates an inspection data communication system. The inspection data communication can be between inspection device 412 and upstream slave device 411 or between inspection device 412 and downstream slave device 413. The terms upstream indicates that sample pass through the slave device before passing through the inspection device 412. The term downstream indicates that samples pass through the inspection device 412 before passing through the salve device.

It is noted herein, that a slave device is any device located along the sample processing line. Examples of a slave devices includes, but is not limited to: a sorting device, a mixing device, a display device, a sizing device, a blanching device, a feeding device, a cutting, a slicing device, a baking device, a drying device, a freezing device, a coating device, a washing device.

In one scenario, a sample passes through the slave device 411 and then passes through the inspection device 412. Within the inspection device 412, the optical device 404 of the inspection device 400 is triggered by the processor 401 to capture an image. The triggering by the processor 401 is executed when a sample is within the field of view of the optical device 404. The image captured by the optical device 404 is then stored into storage device 402. The processor 401 then processes the captured image and determines one or more quality characteristics of the sample in the captured image. Many different quality characteristics may be determined from the captured image. Some examples of possible quality characteristics includes, but are not limited to: shape quality (based on matching a predetermined shape within a specified tolerance, then the sample is determined to be defective with respect to shape), surface contour quality (when a flat surface is greater than a specified area, then the sample is determined to be defective with respect to surface contour), hole quality (presence of holes in the sample), pest quality (presence of insects in/or on the sample), color quality (irregular color of the sample), size quality (irregular size of the sample), moisture level, oil content, fat content, and mycotoxin content. In one example, a group of quality characteristics are referred to as inspection data 415. FIG. 18, FIG. 19, and FIG. 20 illustrate various examples of inspection data. Communication medium 417 can be a wired medium such as ethernet or RS-232. Alternatively, communication medium 417 can be wireless medium such as WiFi (802.11) or a cellular link. The inspection data 415 is then communicated to slave device 411. In this fashion, the slave device 411 can then analyze the inspection data and adjust the operation of slave device 411 such that more desirable samples are output from slave device 411. This scenario requires that slave device 411 include some local knowledge and processing capability to analyze the received inspection data and to adjust the operations of the slave device 411 based on the analysis.

It is noted herein, the inspection device 400 illustrated in FIG. 13 is only one example of an inspection device. Another example of an inspection device is the in-flight 3D inspector 1 illustrated in FIGS. 1-5.

It is also noted herein, that multiple samples may be within the field of view of the optical device 404 when an image is captured and therefore quality characteristics of multiple samples may be determined using a single captured image.

In another scenario, a sample passes through the inspection device 412 and then passes through the slave device 413. Within the inspection device 412, the optical device 404 of the inspection device 400 is triggered by the processor 401 to capture an image. The triggering by the processor 401 is executed when a sample is within the field of view of the optical device 404. The image captured by the optical device 404 is then stored into storage device 402. The processor 401 then processes the captured image and determines one or more quality characteristics of the sample in the captured image. Many different quality characteristics may be determined from the captured image. In one example, multiple quality characteristics are referred to as inspection data 415. The inspection data 415 is then communicated to slave device 413 via communication medium 417. Communication medium 417 can be a wired medium such as ethernet or RS-232. Alternatively, communication medium can be wireless medium such as WiFi (802.11) or cellular link In this fashion, the slave device 413 can then analyze the inspection data and adjust the operation of slave device 413 such that more desirable samples are output from slave device 413. This scenario requires that slave device 413 include some local knowledge and processing capability to analyze the received inspection data and to adjust the operations of the slave device 413 based on the analysis.

While the scenario illustrated in FIG. 14 provides the slave devices 411 and 413 with the most control over how they operate, in many instances slave devices 411 and 413 will not have the necessary knowledge and processing power to analyze the inspection data generated by the inspection device 412. This problem is addressed by moving the processing of the inspection data to the inspection device 412. This solution is illustrated in FIG. 15.

Figure 15:
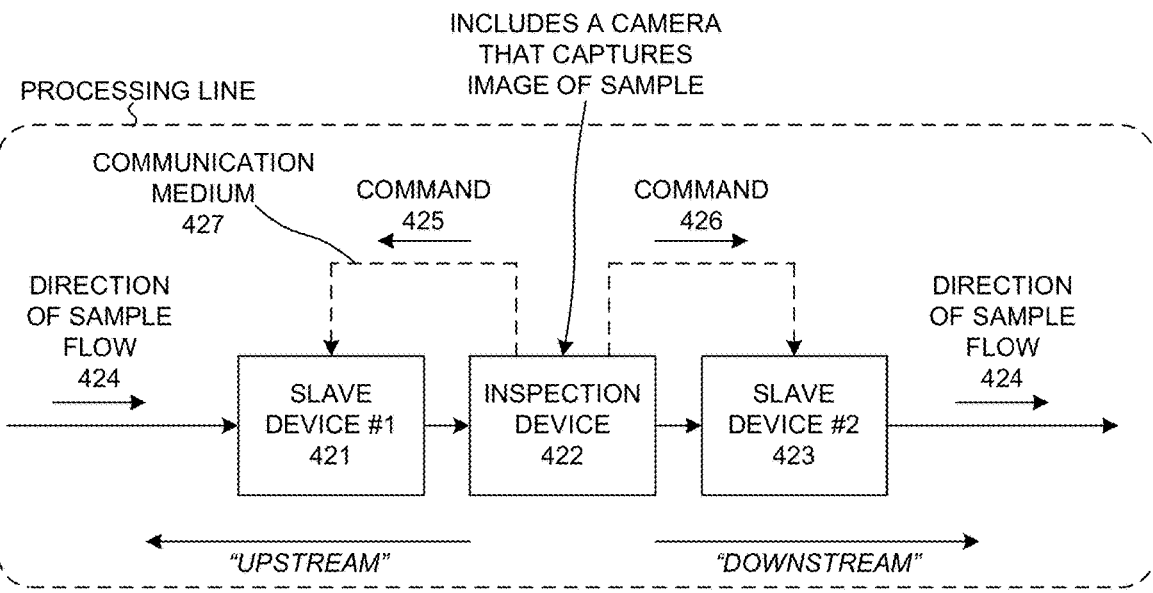
FIG. 15 is a diagram of a command communication system.
Figure 21:
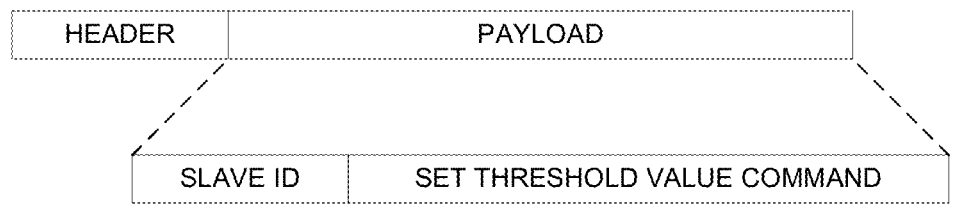
FIG. 21 is a diagram of a first example of a command based on inspection data.
Figure 22:
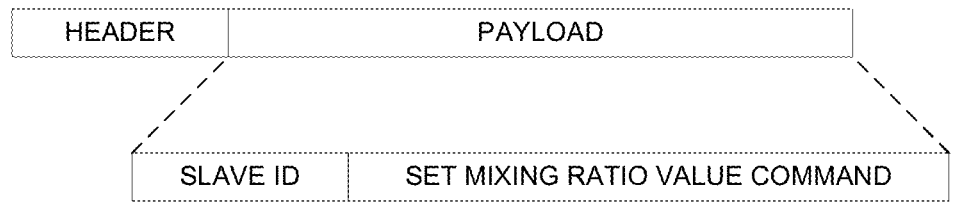
FIG. 22 is a diagram of a second example of a command based on inspection data.
Figure 23:
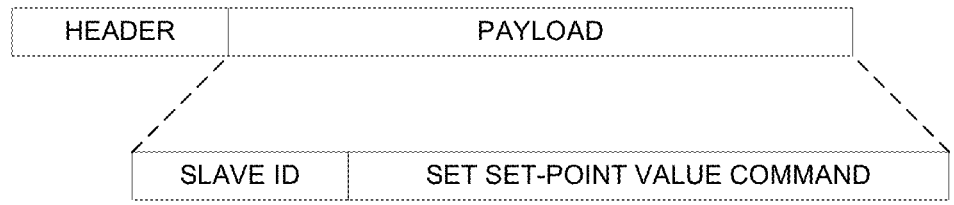
FIG. 23 is a diagram of a third example of a command based on inspection data.

FIG. 15 illustrates a command communication system. The terms upstream indicates that sample pass through the slave device before passing through the inspection device 422. The term downstream indicates that samples pass through the inspection device 422 before passing through the slave device. In this system, a sample passes through the slave device 411 and then passes through the inspection device 412. Within the inspection device 412, the optical device 404 of the inspection device 400 is triggered by the processor 401 to capture an image. The triggering by the processor 401 is executed when a sample is within the field of view of the optical device 404. The image captured by the optical device 404 is then stored into storage device 402. The processor 401 then processes the captured image and determines one or more quality characteristics of the sample in the captured image. In one example, multiple quality characteristics are referred to as inspection data. Instead of communicating the raw inspection data to the slave device 421, the inspection device 422 performs the analysis of the inspection data and generates a command 425 to adjust the operation of slave device 421. FIG. 21, FIG. 22, and FIG. 23 illustrate various examples of commands that are generated based on inspection data. For example, a command may be to set a threshold value to be used by a slave device. In another example, a command may be to set a mixing ratio value in a slave device. In yet another example, the command may be to adjust a set-point value in a slave device. The command 425 is then communicated to slave device 421 via communication medium 427. Slave device 421 then adjusts operation as commanded such that more desirable samples are output from slave device 421. This scenario does not require that slave device 421 include some local knowledge and processing capability to analyze inspection data and to adjust the operations of the slave device 421 based on the analysis. Rather, this scenario does not require any local knowledge or processing capability to be present on the slave device 421, because all the necessary analysis is performed by the inspection device 422. Slave device 421 can operate as a "dumb" terminal that simply adjusts operation based on received commands from the inspection device 422. This solution may be very valuable as it reduces the number of devices that are required to have local processing capability and knowledge, which in turn reduces the cost of the overall system.

In another scenario, a sample passes through the inspection device 422 and then passes through the slave device 423. Within the inspection device 412, the optical device 404 of the inspection device 400 is triggered by the processor 401 to capture an image. The triggering by the processor 401 is executed when a sample is within the field of view of the optical device 404. The image captured by the optical device 404 is then stored into storage device 402. The processor 401 then processes the captured image and determines one or more quality characteristics of the sample in the captured image. In one example, multiple quality characteristics are referred to as inspection data. Instead of communicating the raw inspection data to the slave device 423, the inspection device 422 performs the analysis of the inspection data and generates a command 426 to adjust the operation of slave device 423. The command 426 is then communicated to slave device 423 via a communication medium. Slave device 423 then adjusts operation as commanded such that more desirable samples are output from slave device 423. This scenario does not require that slave device 423 include some local knowledge and processing capability to analyze inspection data and to adjust the operations of the slave device 423 based on the analysis. Rather, this scenario does not require any local knowledge or processing capability to be present on the slave device 423, because all the necessary analysis is performed by the inspection device 422. Slave device 423 can operate as a "dumb" terminal that simply adjusts operation based on received commands from the inspection device 422. This solution may be very valuable as it reduces the number of devices that are required to have local processing capability and knowledge, which in turn reduces the cost of the overall system.

Figure 16:
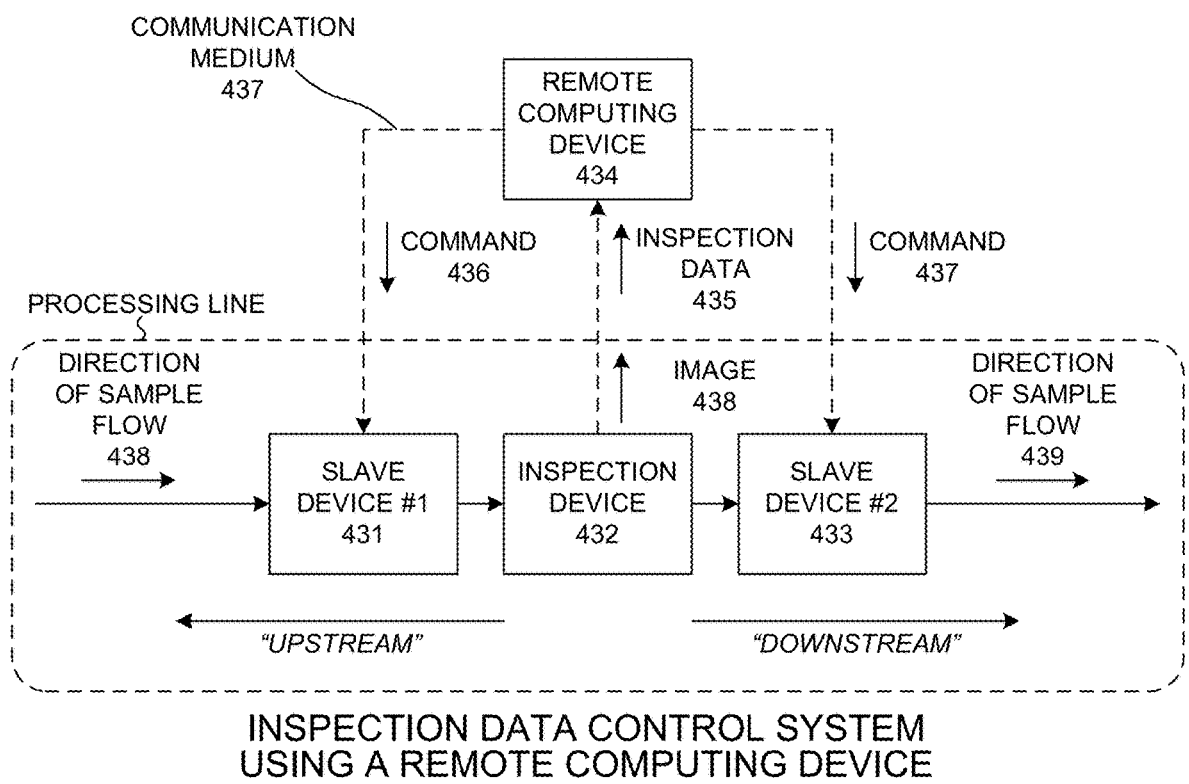
FIG. 16 is a diagram of an inspection data control system using a remote computing device.

While the scenario illustrated in FIG. 15 provides cost saving by only requiring a single device in the system to have the necessary knowledge and processing power, it may be even more advantageous if the none of the devices in the system are required to have local processing capability and knowledge to analyze the captured images. FIG. 16 illustrates an inspection data control system using a remote computing device.

FIG. 16 illustrates an inspection data control system using a remote computing device. The terms upstream indicates that sample pass through the slave device before passing through the inspection device 432. The term downstream indicates that samples pass through the inspection device 432 before passing through the salve device. In this system, a sample passes through the slave device 431 and then passes through the inspection device 432. Within the inspection device 432, the optical device 404 of the inspection device 400 is triggered by the processor 401 to capture an image 438. The triggering by the processor 401 is executed when a sample is within the field of view of the optical device 404. The image 438 captured by the optical device 404 is then stored into storage device 402. The processor 401 does not process the captured image 438 to determine one or more quality characteristics of the sample in the captured image 438. Rather, the inspection device 432 communicates the captured image 438 to a remote computing device 434. In one example, remote computing device 434 is a remote computer or server that is not part of any machine through which the sample flows. In response to receiving the captured image 438, the remote computing device 434 performs the analysis of the captured image 438 and generates a command 436 to adjust the operation of slave device 431. The command 436 is then communicated to slave device 431 via communication medium 437. Slave device 431 then adjusts operation as commanded such that more desirable samples are output from slave device 431. This scenario does not require any local knowledge or processing capability to be present on the slave device 431, because all the necessary analysis is performed by the remote computing device 434. Likewise, this scenario does not require any local knowledge or processing capability to be present on the inspection device 432, because all the necessary analysis is performed by the remote computing device 434. Both slave device 431 and inspection device 432 can operate as "dumb" terminals that simply adjust operation based on received commands from the remote computing device 434. This solution may be very valuable as it does not require any devices through which the sample passes to have local processing capability and knowledge, which in turn reduces the cost of the overall system.

In another scenario, a sample passes through the inspection device 432 and then passes through the slave device 433. Within the inspection device 432, the optical device 404 of the inspection device 400 is triggered by the processor 401 to capture an image 438. The triggering by the processor 401 is executed when a sample is within the field of view of the optical device 404. The image 438 captured by the optical device 404 is then stored into storage device 402. The processor 401 does not process the captured image 438 to determine one or more quality characteristics of the sample in the captured image. Rather, the inspection device 432 communicates the captured image 438 to a remote computing device 434. In one example, remote computing device 434 is a remote computer or server that is not part of any machine through which the sample flows. In response to receiving the captured image 438, the remote computing device 434 performs the analysis of the captured image 438 and generates a command 437 to adjust the operation of slave device 433. The command 437 is then communicated to slave device 433 via communication medium. Slave device 433 then adjusts operation as commanded such that more desirable samples are output from slave device 433. This scenario does not require any local knowledge or processing capability to be present on the slave device 433, because all the necessary analysis is performed by the remote computing device 434. Likewise, this scenario does not require any local knowledge or processing capability to be present on the inspection device 432, because all the necessary analysis is performed by the remote computing device 434. Both slave device 433 and inspection device 432 can operate as "dumb" terminals that simply adjust operation based on received commands from the remote computing device 434. This solution may be very valuable as it does not require any devices through which the sample passes to have local processing capability and knowledge, which in turn reduces the cost of the overall system.

In another example, captured image 438 is not communicated from the inspection device 432 to the remote computing device 434, but rather inspection data 435 is communicated from the inspection device 432 to remote computing device 434. In this scenario, the inspection device 432 captures an image of the sample and from the captured image determines quality characteristic(s) of the sample. The inspection data (grouping of quality characteristics) is then communicated to the remote computing device 434. In response to receiving the inspection data, the remote computing device 434 generates one or more commands to adjust one or more slave devices. In this example, the inspection device 432 requires the processing capability to determine the quality characteristics, but does not require the capability to determine commands for adjusting slave devices.

While the scenario illustrated in FIG. 16 a great improvement, a remote computing device can be used in an even more beneficial way. This improved use is illustrated in FIG. 17.

Figure 17:
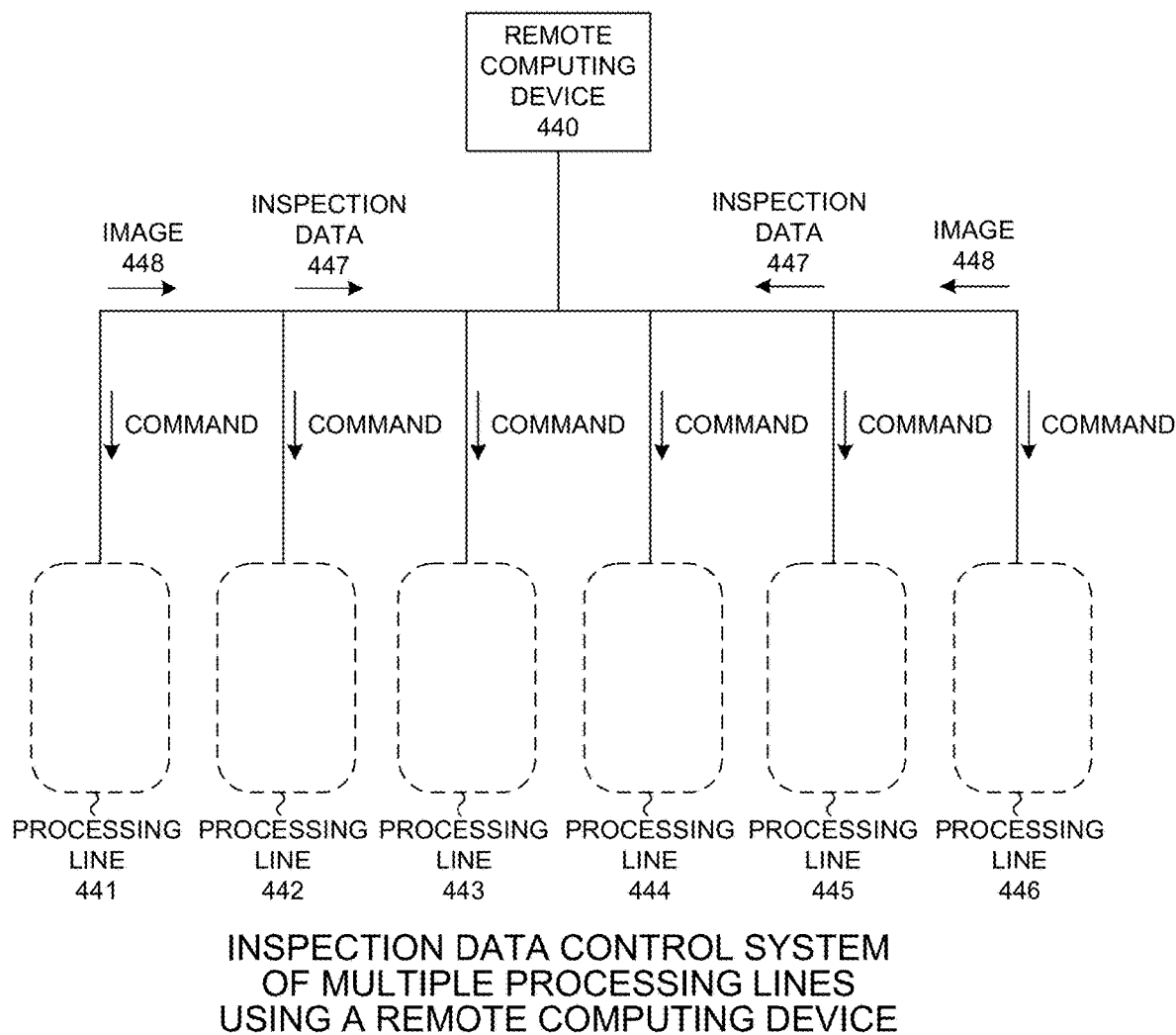
FIG. 17 is a diagram of an inspection data control system of multiple processing lines using a remote computing device.

FIG. 17 illustrates an inspection data control system of multiple processing lines using a remote computing device. Each processing line 441-446 includes at least one inspection device that is capable of capturing an image and sending the capture image and/or inspection data based on the captured image to a remote computing device 440.

The in response to receiving only the captured image data 448, the remote computing device 440 determines quality characteristics and then based on those quality characteristics ("inspection data") the remote computing device 440 generates command(s) to adjust the operation of slave device(s) in the processing line from which the image was captured.

In response to receiving the inspection data 447, the remote computing device 440 generates command(s) to adjust the operation of slave device(s) in the processing line from which the image was captured.

This scenario also reduces the complication of managing multiple sample processing lines. A single remote computing device 440 could receive inspection data from various inspection devices included in various processing lines 441-446. In this fashion, the single remote computing device 440 could monitor and adjust all the various slave devices in processing lines 441-446. This scenario can also provide for advanced learning because all inspection data from all processing lines 441-446 are received by the remote computing device 440, which in turn allows for improved artificial intelligence learning by way of access to larger sets of relevant inspection data.

This scenario also allows for real-time monitoring and adjusting of multiple processing lines located at various locations around the world.

Figure 24:
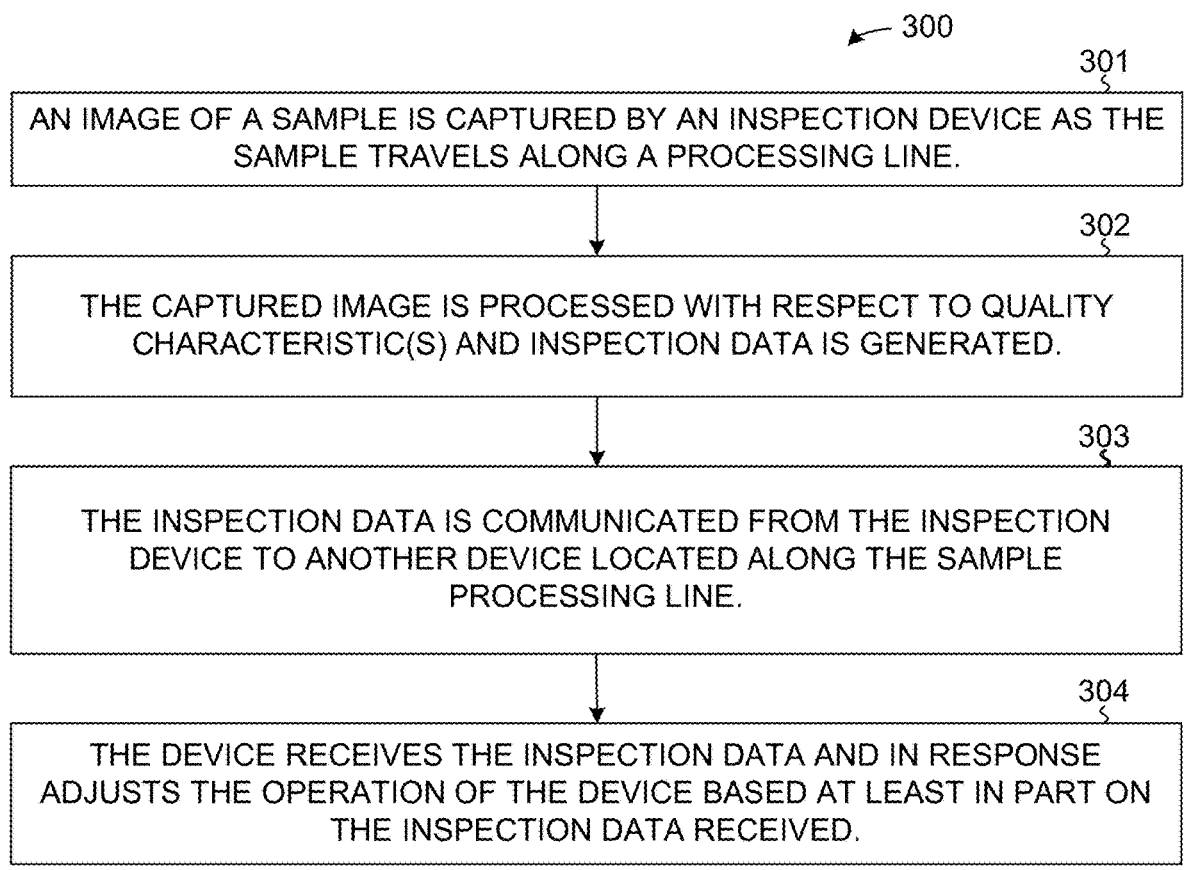
FIG. 24 is a flowchart illustrating the operation of an inspection data communication system.

FIG. 24 is a flowchart 300 of an inspection data communication system. In step 301, an image of a sample is captured by an inspection device as the sample travels along a processing line. In step 302, the captured image is processed with respect to quality characteristic(s) and inspection data is generated. In step 303, the inspection data is communicated from the inspection device to another device located along the sample processing line. In step 304, the device receives the inspection data and in response adjusts the operation of the device based at least in part on the inspection data received.

Figure 25:
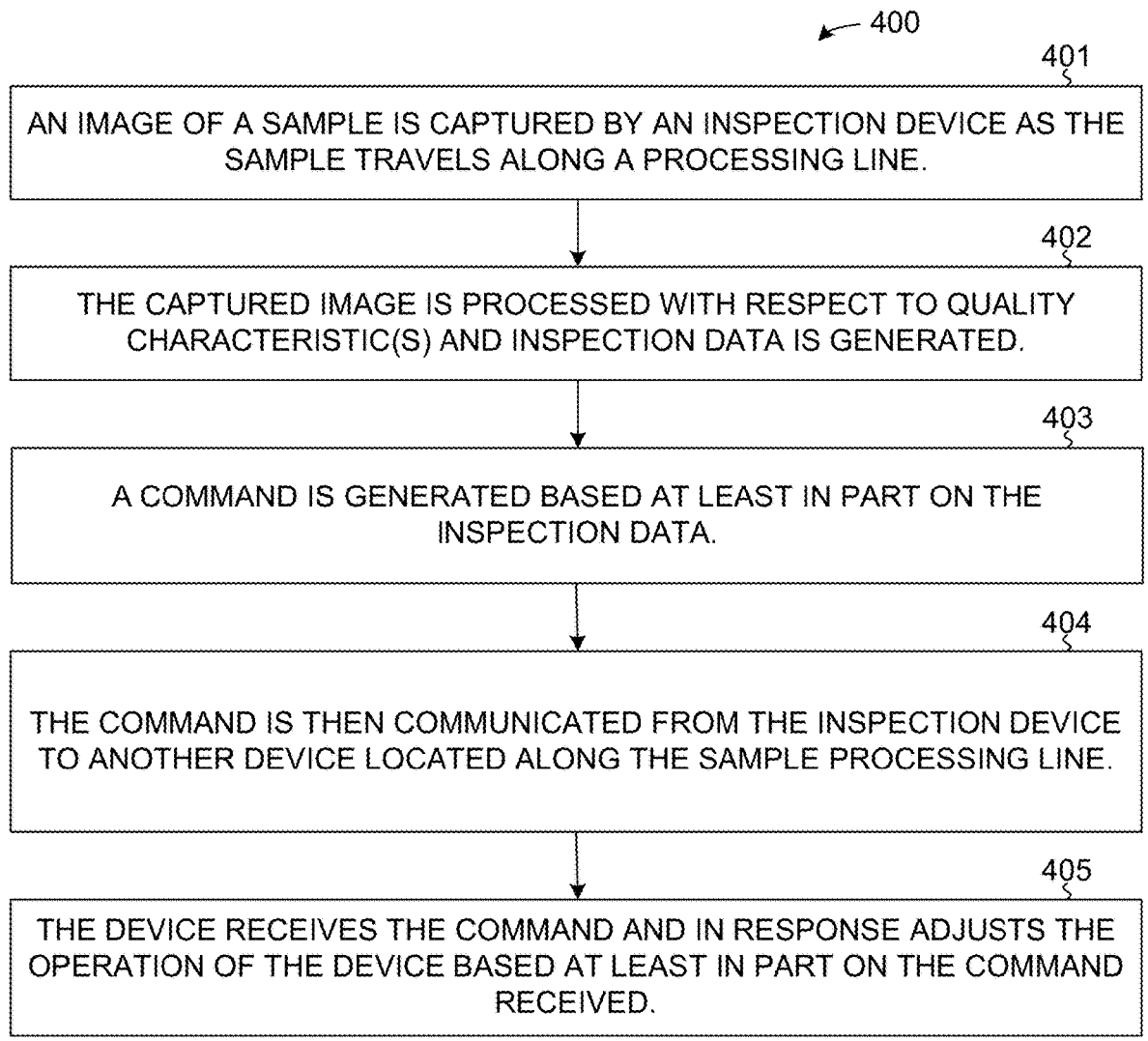
FIG. 25 is a flowchart illustrating the operation of a command communication system.

FIG. 25 is a flowchart 400 of a command communication system. In step 401, an image of a sample is captured by an inspection device as the sample travels along a processing line. In step 402, the captured image is processed with respect to quality characteristic(s) and inspection data is generated. In step 403, a command is generated based at least in part on the inspection data. In step 404, the command is then communicated from the inspection device to another device located along the sample processing line. In step 405, the device receives the command and in response adjusts the operation of the device based at least in part on the command received.

Figure 26:
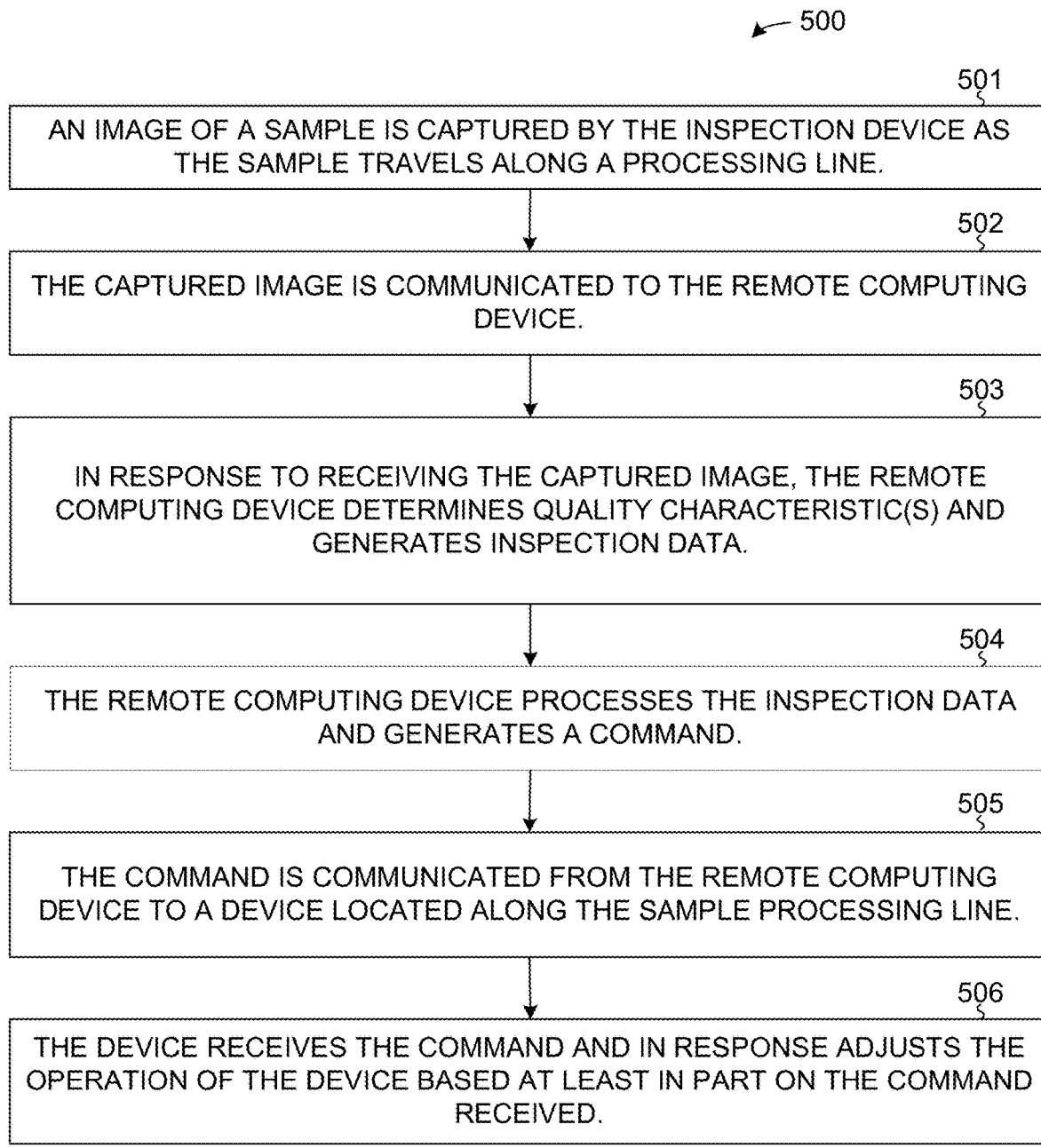
FIG. 26 is a flowchart illustrating a first example of the operation of an inspection data communication system using a remote computing device.

FIG. 26 is a flowchart 500 of an inspection data control system using a remote computing device. In step 501, an image of a sample is captured by the inspection device as the sample travels along a processing line. In step 502, the captured image is communicated to the remote computing device. In step 503, in response to receiving the captured image, the remote computing device determines quality characteristic(s) and generates inspection data. In step 504, the remote computing device processes the inspection data and generates a command. In step 505, the command is communicated from the remote computing device to a device located along the sample processing line. In step 506, the device receives the command and in response adjusts the operation of the device based at least in part on the command received.

Figure 27:
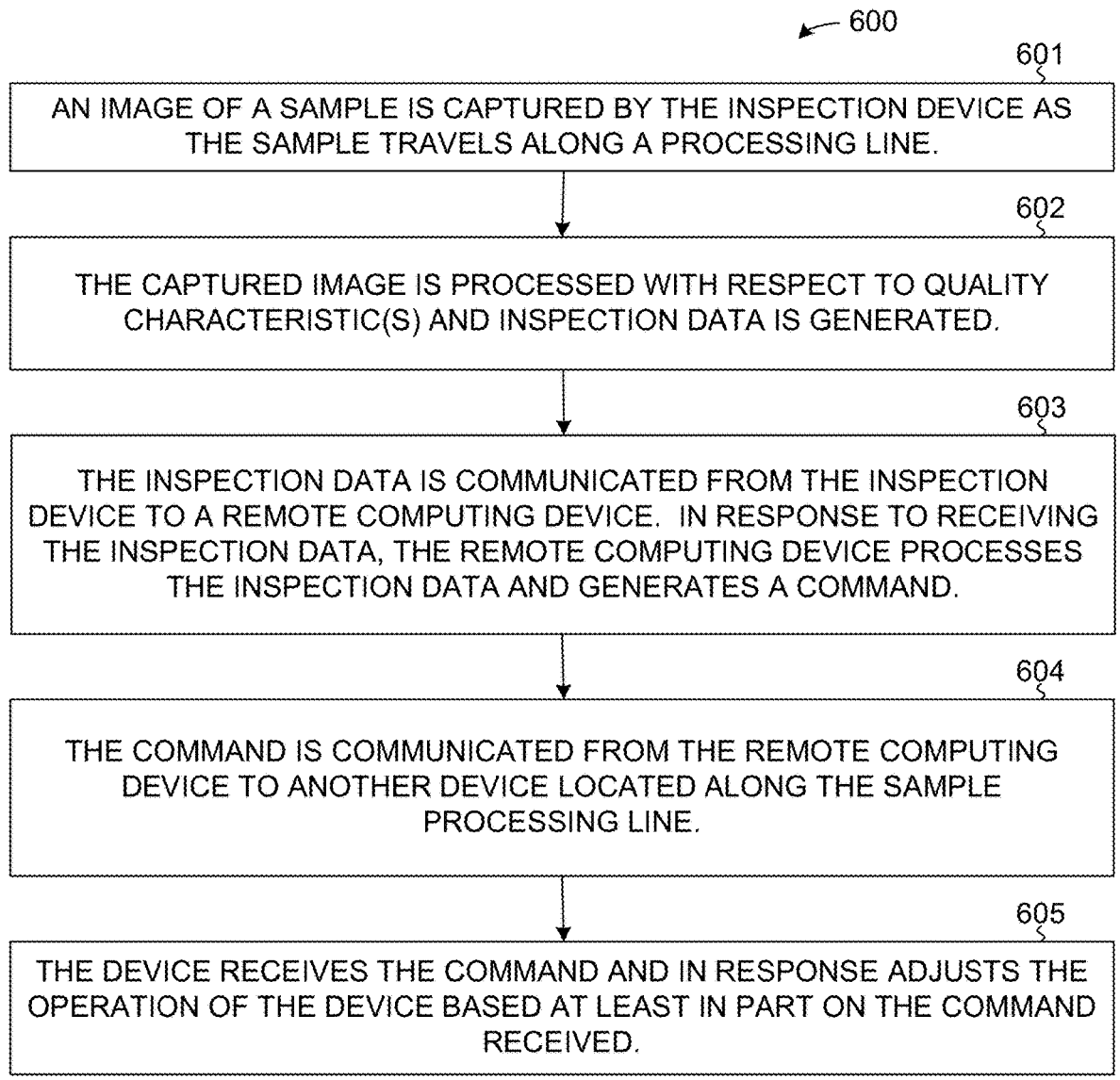
FIG. 27 is a flowchart illustrating a second example of the operation of an inspection data communication system.

FIG. 27 is a flowchart 600 of an inspection data control system using a remote computing device. In step 601, an image of a sample is captured by the inspection device as the sample travels along the processing line. In step 602, the captured image is processed with respect to quality characteristic(s) and inspection data is generated. In step 603, the inspection data is communicated from the inspection device to a remote computing device and in response to receiving the inspection data, the remote computing device processes the inspection data and generates a command. In step 604, the command is communicated from the remote computing device to another device located along the sample processing line. In step 605, the device receives the command and in response adjusts the operation of the device based at least in part on the command received.

Distributed Ledger

A distributed ledger, sometimes referred to as "Blockchain", is a shared public ledger on which a system relies. The distributed ledger has a linked list data structure, with each block containing a hash of the previous block. Each block is formed by a proof-of-work algorithm, through which consensus of this distributed ledger could be obtained via the longest possible chain. The distributed ledger provides the basis for a distributed system that does not require trust between various users and is extendable in many ways through modifications of the parameters of the chain.

A block is an aggregated set of data. Data are collected and processed to fit in a block through a process called mining. Each block could be identified using a cryptographic hash (also known as a digital fingerprint). The formed block will contain a hash of the previous block, so that blocks can form a chain from the first block ever (known as the Genesis Block) to the newly formed block. In this way, all the data could be connected via a linked list structure.

Data are contained inside blocks as well as an arbitrary integer (called nounce) that is necessary for producing the proof-of-work. In the example of Bitcoin, a block contains a header and relevant transaction data. A merkle tree of transactions is created and the hash of the root is included in the header. A merkle tree is a full binary tree of a hash values. At the bottom level of the tree, each transaction has a node containing its hash value. The tree is constructed in a way such that the parent node has a value of the hash of the data contained in its children concatenating together. The merkle tree data structure allows fast validation by constructing a merkle tree path from the bottom level of the tree up to the root node. Since each bitcoin transaction output can be spent only once, as long as the output is spent, it could be erased out of the tree structure using some pruning algorithms. In this way, disk usage is reduced while the validation functions are preserved.

Various blocks in the blockchain are connected to specific other blocks in the blockchain. In one example, each block contains a hash of its previous block. In bitcoin blockchain for example, the block header has a field for previous block hash. Therefore all blocks will contain a reference of its previous block thereby enabling the chain to be build up to the genesis block.

A fork on the block chain may occur. A fork in the block chain occurs due to two blocks computed at a very short time interval. The subsequent blocks may build upon both blocks and both of the chains remain valid. In subsequent process of mining, one fork would be longer than the other fork, in this case, the longer chain would be accepted by the network and the short would not be used unless its length exceeds the longer chain in the future.

Many distributed ledgers, such as Bitcoin blockchain, use a proof-of-work algorithm for reaching a consensus. The cryptographic hash function of each block must be smaller than a specific value in order to be considered value. A nonce is therefore included in the block for this feature. By using the proof-of-work method, in order to change the data in one block, all successors of that block must be re-written and a huge amount of calculation is necessary. In addition, the longest chain would be accepted by the network whereas the shorter ones would be discarded at the situation of branches of the chain. This makes the data in blocks practically unmodifiable. Further, the more blocks that are built upon the block in which the data is contained, more processing is required to overwrite the data.

However, the blockchain may use other methods of consensus. For example, a blockchain may use Scrypt for proof-of-work algorithm instead of hash functions. In addition, the blockchain could be extended for scientific computation where a correct solution to a certain problem could act a validation method. In this way, the computation power may be used to help solving scientific problems and contribute to scientific researches.

In a distributed ledger, each user running a full node on the computer will download a full copy of the whole blockchain, which will include data of all events, such as transactions, recorded on the blockchain. After that, each node can run independently to process any incoming events, such as transactions, and propagate the event further. The node can also contribute to the establishment of the consensus by mining to include event data in a block and then to find a proof-of-work for the block. There is not a central node processing the data and distributing the data, rather every node can run independently and broadcast any work that is proved. This model of distributed computation could be extended to many other services such as Domain Name Server.

Quality Inspection Data Distributed Ledger

While distributed ledgers have been utilized to perform financial transactions, distributed ledgers have not been utilized to perform recordation and distribution of quality inspection data.

Quality inspection data is measured and recorded for many different items around the world, such as pharmaceuticals, mechanical hardware, agricultural foods and many, many more.

One challenge is the acquisition of quality inspection data. For example, some quality inspection data is generated by humans reviewing items manually. This process is prone to large variances depending on the human conducting the inspection as well as the state of the human when the inspection is conducted. In other examples, computer automation is used to help, or entirely, acquire the quality inspection data as disclosed above.

Regardless of the method in which the quality inspection data is acquired, a second challenge is the integrity of the quality data that is reported to interested parties, such as owners, purchasers, manufacturers, etc. For example, in the almond industry many purchasers are weary of the quality data that is alleged by various almond providers. The uncertainty spawns from various sources. First, was the quality inspection data reliable? Second, was the quality inspection data accurately managed and is it accurately aligned with the product being offered? Third, was the quality inspection data intentionally tampered with to increase the market price of the product being sold? Fourth, difficulty to gain access to the data regardless of the three concerns listed above. All of these uncertainties lead to time and cost inefficiencies. A trust worthy, reliable and cost efficient solution is provided herein.

Regarding the reliability of the quality inspection data, as discussed above, an automated system such as the in-flight optical inspector can be used to acquire reliable and consistent quality inspection data.

Regarding the management, possible tampering, and access to the acquired quality inspection data a new quality inspection data distributed ledger is disclosed. This quality inspection data distributed ledger does not perform financial transactions. Rather, the quality inspection data distributed ledger validates the source, timing, product association, and integrity of the quality inspection data.

Figure 28:
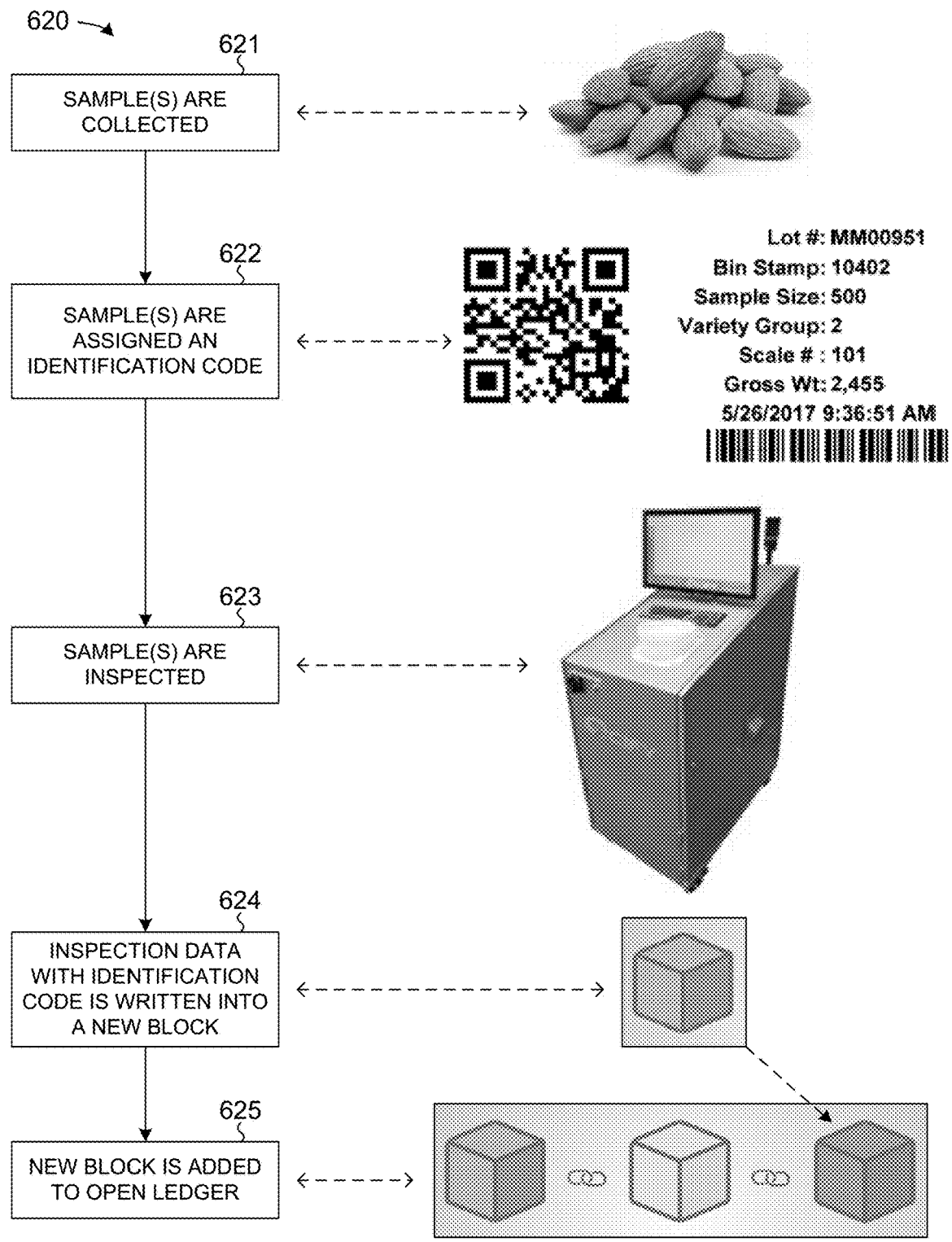
FIG. 28 is a quality inspection data distributed ledger flowchart.

FIG. 28 is a diagram of a quality inspection data distributed ledger flowchart 620. In step 621, one or more samples to be inspected are collected. In step 622, the one or more samples are assigned a unique identification code. In one example, the identification code is affixed to a container containing the one or more samples. In another example, the code is affixed to the one or more samples themselves. The code may be communicated by use of a Quick Response (QR) code, a bar code, printed text, Radio Frequency Identification (RFID) tag, human manual entry, a Near Field Communication (NFC) signal, a token, or any other method of communication known to one of skill in the art.

Once the identification code has been assigned to the one or more samples, the one or more samples are inspected in step 623. This inspection can be performed by any possible method. In one example, the inspection can be performed by human inspection. In another example, the inspection can be performed by an automated inspection. In yet another example, the inspection can be performed by an in-flight 3D inspector as disclosed above.

Upon completion of the inspection of the one or more samples, in step 624 the resulting inspection data and the identification code are written into a new quality inspection data block. An example of a quality inspection data block is illustrated in FIG. 29. The exemplary quality inspection data block of FIG. 29 may include the following data fields: an inspection entity that conducted the inspection, inspection location where the inspection was conducted, the sensor identification number that identifies the sensor or inspection device that performed the inspection, the lot number of the one or more samples, the total weight of the lot of samples, analysis completion timestamp indicating when the inspection was performed or completed, the amount of product analyzed (for example in weight or quantity), the moisture content of the samples, the kernel size of the samples, the uniformity ratio of the samples (average, median, variance, etc.), the percentage or number of "good" samples or samples that pass all required characteristics, the percentage or number of dissimilar samples, the percentage or number of chipped and scratched samples, the percentage or number of samples including another type of defect, the percentage or number of samples that have serious damage, and the quality grade of the one or more samples, such as U.S. Extra #1 grade.

The exemplary quality inspection data block of FIG. 29 may also include the following data fields: a color value, a microtoxin value (milligram/kg, microgram/kg, Parts Per Million, Parts Per Billion . . . ), a temperature value, an acidity (pH) value, a pressure value (kPA, PSI . . . ), a volume per unit time (cubic meters per second), an amount of discolored product (number of percentage), an amount of broken product (number or percentage), an amount of rancid product (number or percentage), an amount of moldy product (number of percentage), an amount of immature product (number or percentage), an amount of unripe product (number or percentage), or an amount of rotten soft product (number or percentage).

The inspection data fields listed above are only provided to be exemplary. One skilled in the art will appreciate that any other characteristic determined during inspection can be included in the quality inspection data block. Likewise, any of the inspection data fields listed can be omitted from the quality inspection data block as well. A list of other possible inspection devices are listed below.

Optical sensors
Moisture sensors
Microtoxin sensors
Thermometer sensors
Acidity (pH) sensors
Microwave sensors
Pressure sensors
Level sensors
Ultrasonic sensors
Flow sensors
Viscosity sensors
Conductance/Impedance sensors
Electronic Nose (sniffing) sensors
X-ray sensors
Multi Spectral (visual/non visual) sensors
Weight sensors
Refractometers sensors
Tenderometer sensors
Firmness sensors
Hardness sensors
Proximity sensor The quality inspection data block may also include hash information. The quality inspection data block may include any of the following hash information: Hash of the quality inspection data block itself, hash of the previous quality inspection data block, hash of the next quality inspection data block, or a Merkle root.

In the example where an inspector with computational capabilities performs the inspection, the inspector may create the quality inspection data block itself upon completion of the inspection process. In the example where the inspector does not have computational capabilities, the data collected by the inspector can be manually entered into computationally capable device to create the quality inspection data block.

In step 625, after the quality inspection data block is created, the quality inspection data block is added to the distributed ledger. In one example, the distributed ledger is referred to as a blockchain. In the example where an inspector includes networking capabilities, the inspector can add the new quality inspection data block to the distributed ledger via a network. Once the quality inspection data block has been added to the distributed ledger, the quality inspection data block is available for viewing by anyone on the network and cannot easily be changed.

This quality inspection data distributed ledger will solve the problems currently facing the consumers of quality inspection data. Consumers of quality inspection data will now have a single source of trustworthy quality inspection data that is easy to access.

Adaptable Inspection Unit & Adaptable Sorter Unit

Processing lines are widely used to inspect and sort large quantities of a specific item. For example, processing lines are used to inspect and sort eatable items such as fruits and nuts. Alternatively, processing lines are used to inspect and sort pharmaceutical pills. A popular example of a simple processing line is a conveyor processing line where items are propelled through the processing line via a conveyor belt that is wound around the conveyor head pulley and tail pulley. Other examples of processing lines include, but are not limited to, a flume, a roller belt, a shaker (conventional and linear motion), a slide, a chute, a conveyor tube, a bucket elevator, and a screw conveyor. To date, basic processing lines, such as conveyors, have not been adaptable to work with any improved processing devices.

Recent improvements in the area of sample inspection and sorting, as are disclosed above in the present application, have provided tremendous improvements in the areas of reliability of quality inspection data, high accuracy quality inspection data, low cost of quality inspection data, as well as intelligent and automatic dynamic control of sorting devices. Currently, owners and operators of legacy simple processing lines, such as conveyors and chutes, cannot attain these improvements without upgrading their entire processing line without suffering large costs, new process planning and time delays. A solution is needed to provide these improved inspection and sorting technologies in a way that can be easily and cost effectively adapted to a legacy simple processing line. A solution to this need is provided herein.

Figure 30:
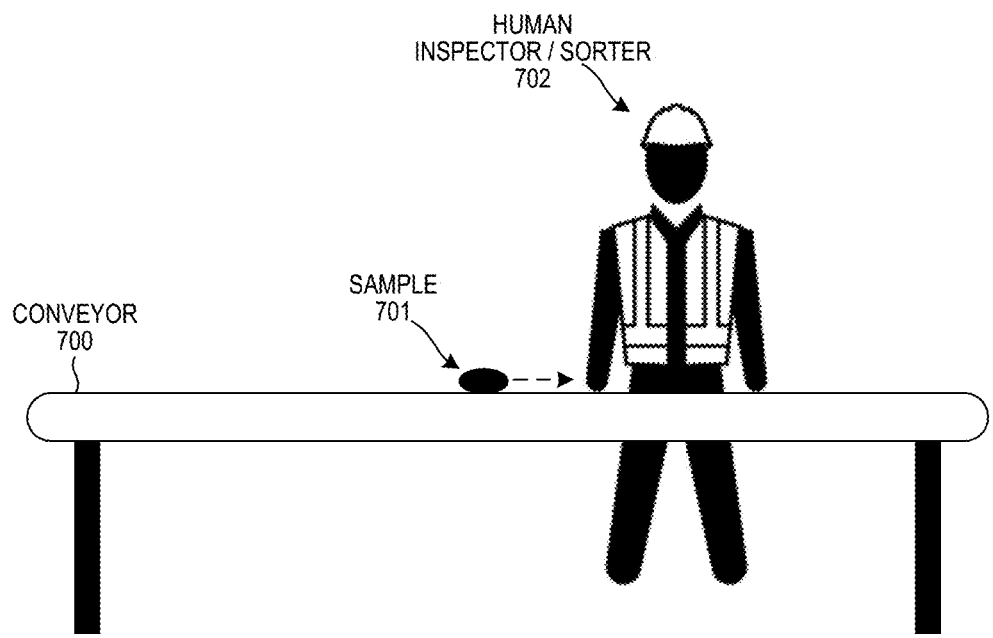
FIG. 30 is a diagram of a conveyor for manual inspection or sorting.

FIG. 30 is a diagram of a conveyor for manual inspection or sorting. This system of using a conveyor for manual inspection and sorting is used widely around the world. In operation, sample 701 is caused to become in contact with conveyor 700. Upon contact, sample 701 is moved via a rotating conveyor belt of conveyor 700. A conveyor belt usually rotates the conveyor belt about two or more pulleys. The friction between the sample and the rotating conveyor belt causes the sample to be move along the direction of the conveyor belt movement. A human is located proximate to the conveyor where the human can see the sample as it travels past the human. In the event that the human needs to more clearly see the sample, the human can pick up and more carefully inspect the sample. The human has the responsibility of determining the quality of the sample. Further, the human has the responsibility to determine how the sample should be sorted based on the determined quality. For example, the human may determine that the sample is of a quality that should be discarded. In which case, the human would manually with the humans hand, or with a tool manually manipulated by the human, cause the sample to be removed from the processing line and sent to a group of discarded samples. In another example, the human may determine that the sample is of a mediocre quality that should not be discarded, but also should not be grouped with top quality samples. In which case, the human would manually cause the sample to be moved to a group of mediocre samples. In yet another example, the human may determine that the sample is of top quality. In which case, the human would not cause the sample to be moved at all, but would rather allow the sample to continue through the processing line to be grouped with all other top quality samples. The samples may be fruits, nuts, pills or any other type of item for which quality control is required.

This method requires a large amount of human attention and time. Moreover, this method of manual inspection and sorting is prone to human error, low quality accuracy, and low repeatability (inconsistent results).

Figure 31:
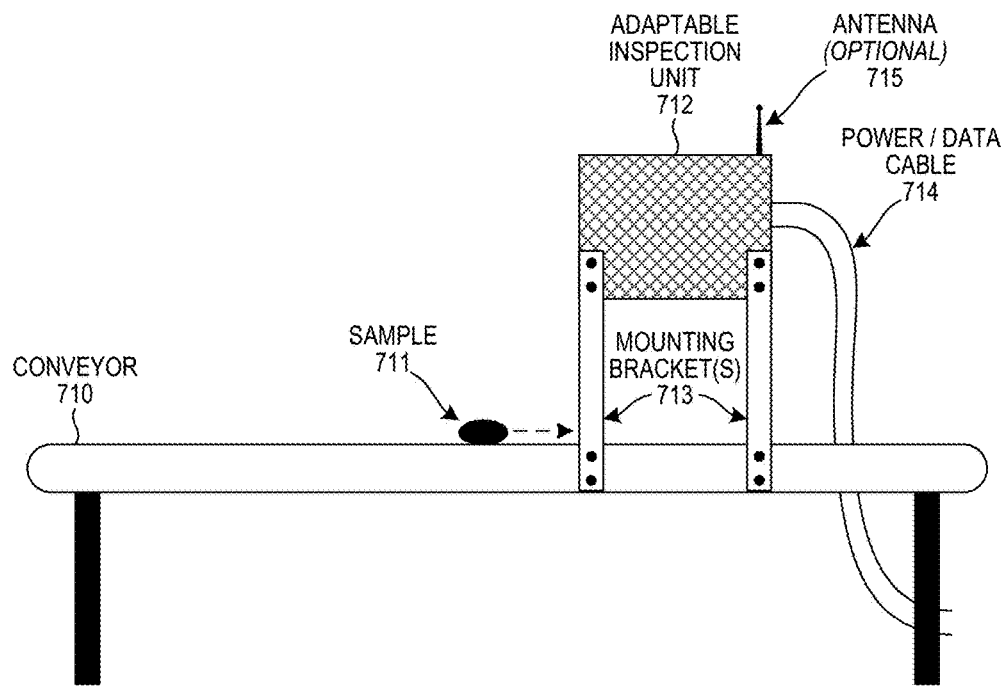
FIG. 31 is a diagram of a conveyor with an adaptable inspection unit attached to the conveyor.

FIG. 31 is a diagram of a conveyor with an adaptable inspection unit attached to the conveyor. Conveyor 710 is the same as conveyor 700, except in that adaptable inspection unit 712 has been physically mounted to conveyor 700. Similar to FIG. 30, in operation, sample 711 is caused to become in contact with conveyor 710. Upon contact, sample 711 is moved via a rotating conveyor belt of conveyor 710. The friction between the sample and the rotating conveyor belt causes the sample to be move along the direction of the conveyor belt movement.

The adaptable inspection unit 712 is attached to the conveyor 710 via one or more mounting brackets 713. One skilled in the art will readily realize that a various number of brackets and various styles of brackets can be used to mount the adaptable inspection unit 712 to conveyor 710. Mounting Bracket 713 can attach to either the adaptable inspection unit 712 or the conveyor 710 using various items, such as bolts, screws, pins, locks, clamps, welds (metals or thermoplastics), adhesive, slots, magnets, rails, gravity or friction.

Figure 39:
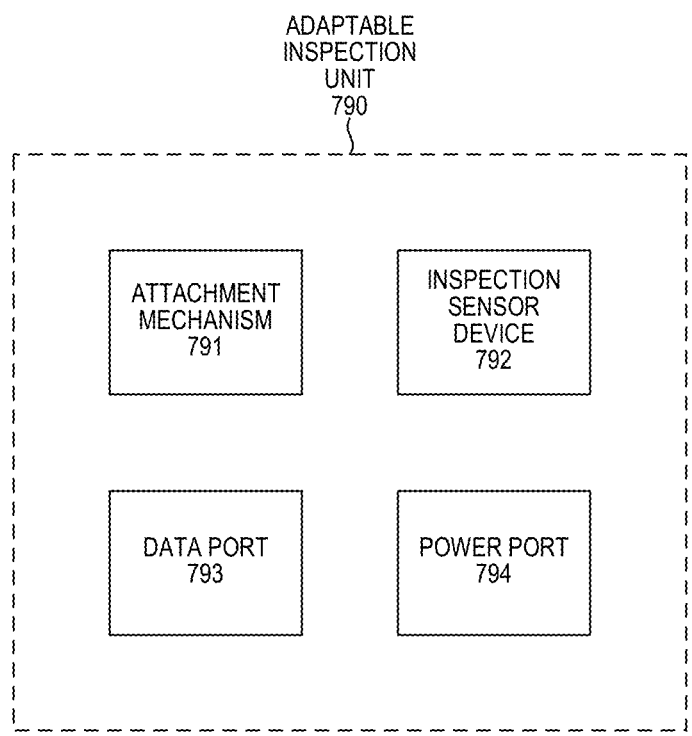
FIG. 39 is a block diagram of an adaptable inspection unit.

The adaptable inspection unit 712 includes an attachment mechanism, an inspection sensor device (optical receiver), a data port and a power port. The data port and the power port may be combined into a single physical port that connects to a single cable 714 that includes both power conductors and data conductors. Alternatively, the adaptable inspection unit 712 may include a data port that is separate from the power port. Further, the adaptable inspection unit 712 may include an antenna connectable data port that connects to an antenna 715 so to allow for wireless communication. FIG. 31 does not illustrate the inspection sensor device. FIG. 39 illustrates a block diagram of an adaptable inspection unit 790 that includes an attachment mechanism 791, an inspection sensor device 792, a data port 793, and a power port 794.

In operation, the conveyor 710 causes the sample 711 to travel under the adaptable inspection unit 712. While the sample is in view of the inspection sensor device that is included in the adaptable inspection unit 712 one or more images of the sample are captured and stored in a memory device. The memory device may be included in the adaptable inspection unit 712 or may be included in a device that communicates with the adaptable inspection unit 712 via the data port (wired or wireless). The captured sensor data (e.g. images) are then processed by a processor executing a quality inspection algorithm. In one example, the adaptable inspection unit 712 includes the 3D inspector described in detail above. In another example, a 3D image of the sample is generated based on the one or more images captured by the adaptable inspection unit 712. In yet another example, the captured 2D image is used to perform the inspection. The 3D or 2D image(s) are used to determine a quality characteristic of the sample. In one example, the quality characteristic is generated by the adaptable inspection unit 712 and output via the data port. In another example, the one or more captured images are output from the adaptable inspection unit 712 to another device that determines the quality characteristics of the sample. Adaptable inspection unit 712 provides improve quality inspection compared to unreliable inspection by human eyes without the cost of replacing an entire processing line. Moreover, adaptable inspection unit 712 is able to inspect many more samples per unit time than could be inspected by a human.

In the example of FIG. 31, all samples are directed toward the same location regardless of measured quality because there is no sorting functionality attached to the conveyor 710.

Figure 32:
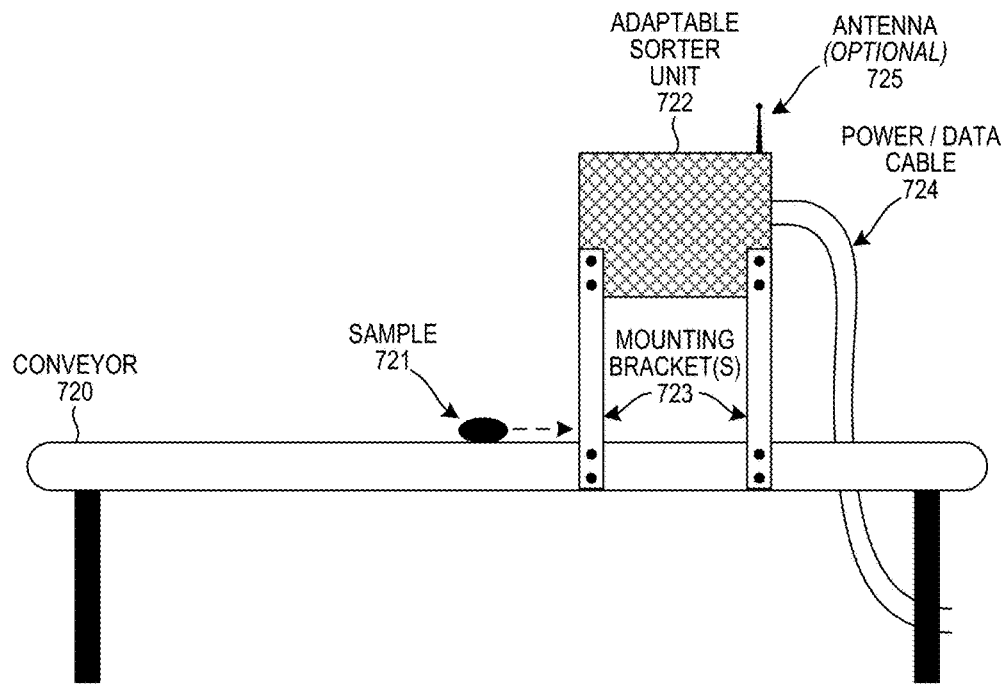
FIG. 32 is a diagram of a conveyor with an adaptable sorting unit attached to the conveyor.

FIG. 32 is a diagram of a conveyor with an adaptable sorting unit attached to the conveyor. Conveyor 720 is the same as conveyor 700, except in that adaptable sorter unit 722 has been physically mounted to conveyor 720. Similar to FIG. 30, in operation, sample 721 is caused to become in contact with conveyor 720. Upon contact, sample 721 is moved via a rotating conveyor belt of conveyor 720. The friction between the sample and the rotating conveyor belt causes the sample to be move along the direction of the conveyor belt movement.

The adaptable sorter unit 722 is attached to the conveyor 720 via one or more mounting brackets 723. One skilled in the art will readily realize that a various number of brackets and various styles of brackets can be used to mount the adaptable sorter unit 722 to conveyor 720. Mounting Bracket 723 can attach to either the adaptable sorter unit 722 or the conveyor 720 using various items, such as bolts, screws, pins, locks, clamps, welds (metals or thermoplastics), adhesive, slots, magnets, rails, gravity or friction.

Figure 40:
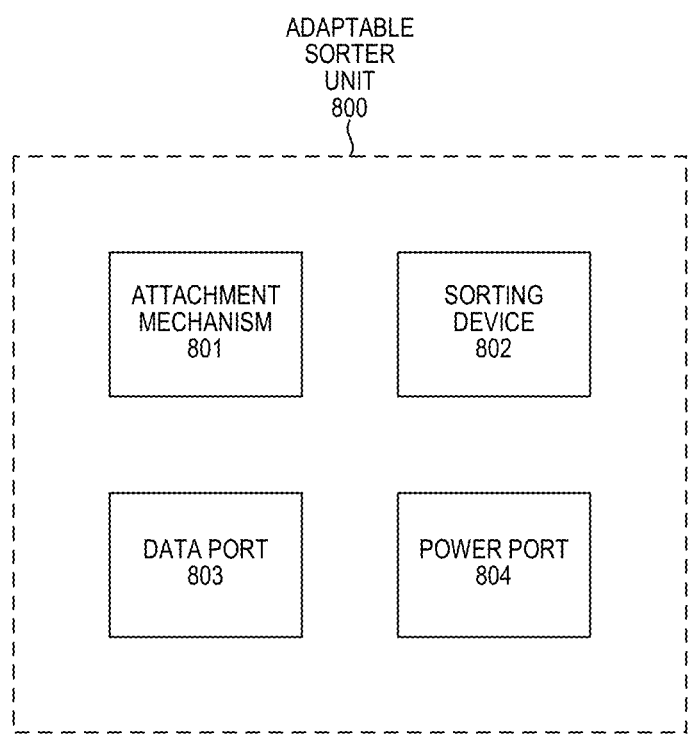
FIG. 40 is a block diagram of an adaptable sorter unit.

The adaptable sorter unit 722 includes an attachment mechanism, a sorting device is capable of deflecting a sample, a data port and a power port. The data port and the power port may be combined into a single physical port that connects to a single cable 724 that includes both power conductors and data conductors. Alternatively, the adaptable sorter unit 722 may include a data port that is separate from the power port. Further, the adaptable sorter unit 722 may include an antenna connectable data port that connects to an antenna 725 so to allow for wireless communication. FIG. 32 does not illustrate the sorting device. FIG. 40 illustrates a block diagram of an adaptable sorter unit 800 that includes an attachment mechanism 801, a sorting device 802, a data port 803, and a power port 804.

In operation, the conveyor 720 causes the sample 721 to travel under the adaptable sorter unit 722. While the sample is in reach of the sorting device that is included in the adaptable sorter unit 722 the sample is sorted as instructed. In one example, the sorting instruction is received via the data port and stored in a memory included in the adaptable sorting unit 722. In another example, quality characteristic data is received via the data port and in response the adaptable sorter unit 722 generates the sorting instruction. In yet another example, the information received via the data port is a percentage of samples to be deflected. Communication with the adaptable sorter unit 722 may be performed via the data port (wired or wireless). The sorting device may be by a vacuum system, a mechanical pedal system, an air jet system, or a mechanical gate. The adaptable sorting unit 722 performs automated sorting so that high quality samples are automatically separated from low quality samples.

Adaptable sorter unit 722 provides improve sorting compared to unreliable sorting by human hands without the cost of replacing an entire processing line. Moreover, adaptable sorter unit 722 is able to sort many more samples per unit time than could be sorted by a human.

Figure 33:
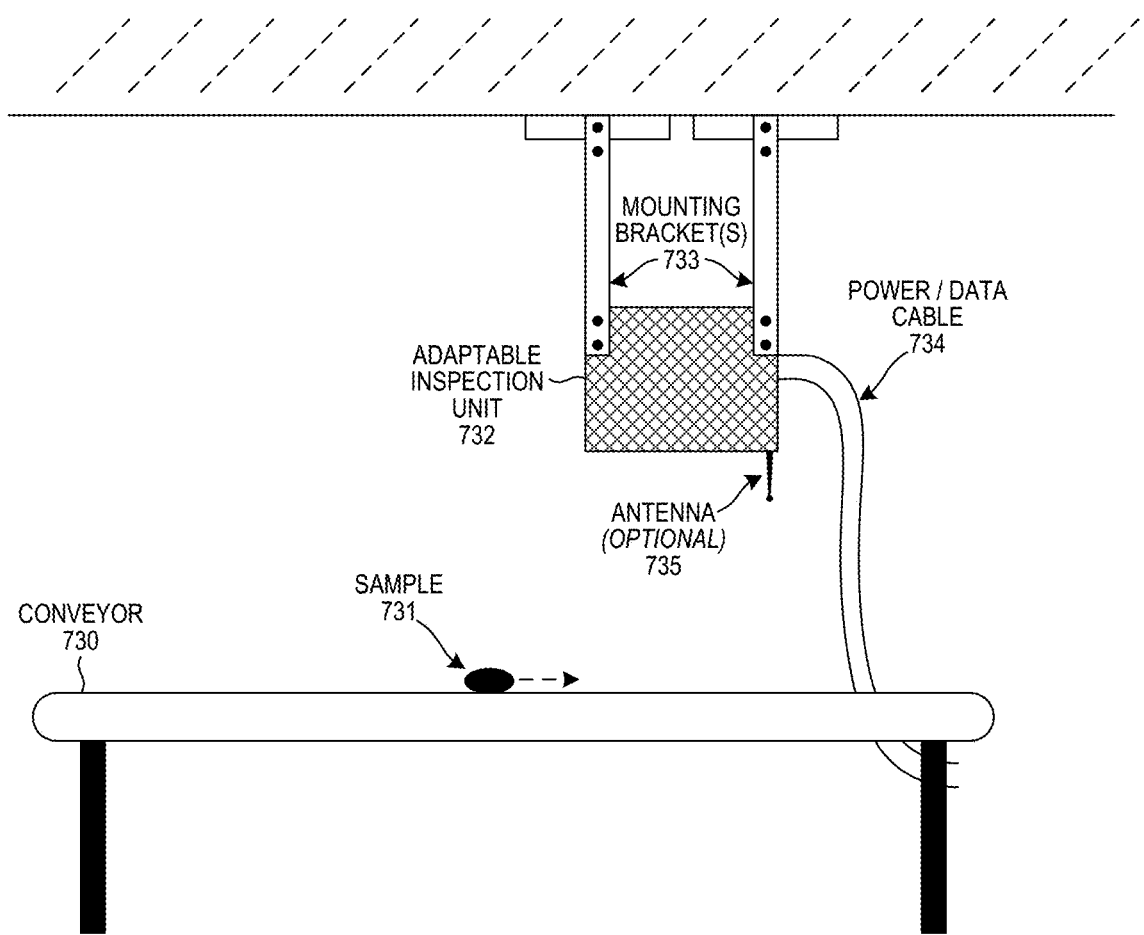
FIG. 33 is a diagram of a conveyor with an adaptable inspection unit attached to the ceiling above the conveyor.

FIG. 33 is a diagram of a conveyor with an adaptable inspection unit attached to the ceiling above the conveyor. Conveyor 730 is the same as conveyor 700, except in that adaptable inspection unit 732 has been physically mounted to the ceiling above conveyor 730. Similar to FIG. 30, in operation, sample 731 is caused to become in contact with conveyor 730. Upon contact, sample 731 is moved via a rotating conveyor belt of conveyor 730. The friction between the sample and the rotating conveyor belt causes the sample to be move along the direction of the conveyor belt movement.

The adaptable inspection unit 732 is attached to the ceiling above conveyor 730 via one or more mounting brackets 733. One skilled in the art will readily realize that a various number of brackets and various styles of brackets can be used to mount the adaptable inspection unit 732 to the ceiling above conveyor 730. Mounting Bracket 733 can attach to either the adaptable inspection unit 712 or the ceiling above conveyor 730 using various items, such as bolts, screws, pins, locks, clamps, welds (metals or thermoplastics), adhesive, slots, magnets, rails, gravity or friction.

The adaptable inspection unit 732 includes an attachment mechanism, an inspection sensor device (optical receiver), a data port and a power port. The data port and the power port may be combined into a single physical port that connects to a single cable 734 that includes both power conductors and data conductors. Alternatively, the adaptable inspection unit 732 may include a data port that is separate from the power port. Further, the adaptable inspection unit 732 may include an antenna connectable data port that connects to an antenna 735 so to allow for wireless communication. FIG. 33 does not illustrate the inspection sensor device. FIG. 39 illustrates a block diagram of an adaptable inspection unit 790 that includes an attachment mechanism 791, an inspection sensor device 792, a data port 793, and a power port 794.

In operation, the conveyor 730 causes the sample 731 to travel under the adaptable inspection unit 732. While the sample is in view, or reach, of the inspection sensor device that is included in the adaptable inspection unit 732 one or more characteristics and/or images of the sample are captured and stored in a memory device. The memory device may be included in the adaptable inspection unit 732 or may be included in a device that communicates with the adaptable inspection unit 732 via the data port (wired or wireless). The captured characteristics and/or image(s) are then processed by a processor executing a quality inspection algorithm. In one example, the adaptable inspection unit 732 includes the 3D inspector described in detail above. In another example, a 3D image of the sample is generated based on the one or more images captured by the adaptable inspection unit 732. In yet another example, the captured 2D image is used to perform the inspection. The 3D and/or 2D image(s) are used to determine a quality characteristic of the sample. In one example, the quality characteristic is generated by the adaptable inspection unit 732 and output via the data port. In another example, the one or more captured images are output from the adaptable inspection unit 732 to another device that determines the quality characteristics of the sample. Adaptable inspection unit 732 provides improve quality inspection compared to unreliable inspection by human eyes without the cost of replacing an entire processing line. Moreover, adaptable inspection unit 732 is able to inspect many more samples per unit time than could be inspected by a human.

In the example of FIG. 33, all samples are directed toward the same location regardless of measured quality because there is no sorting functionality attached to the conveyor 730.

Figure 34:
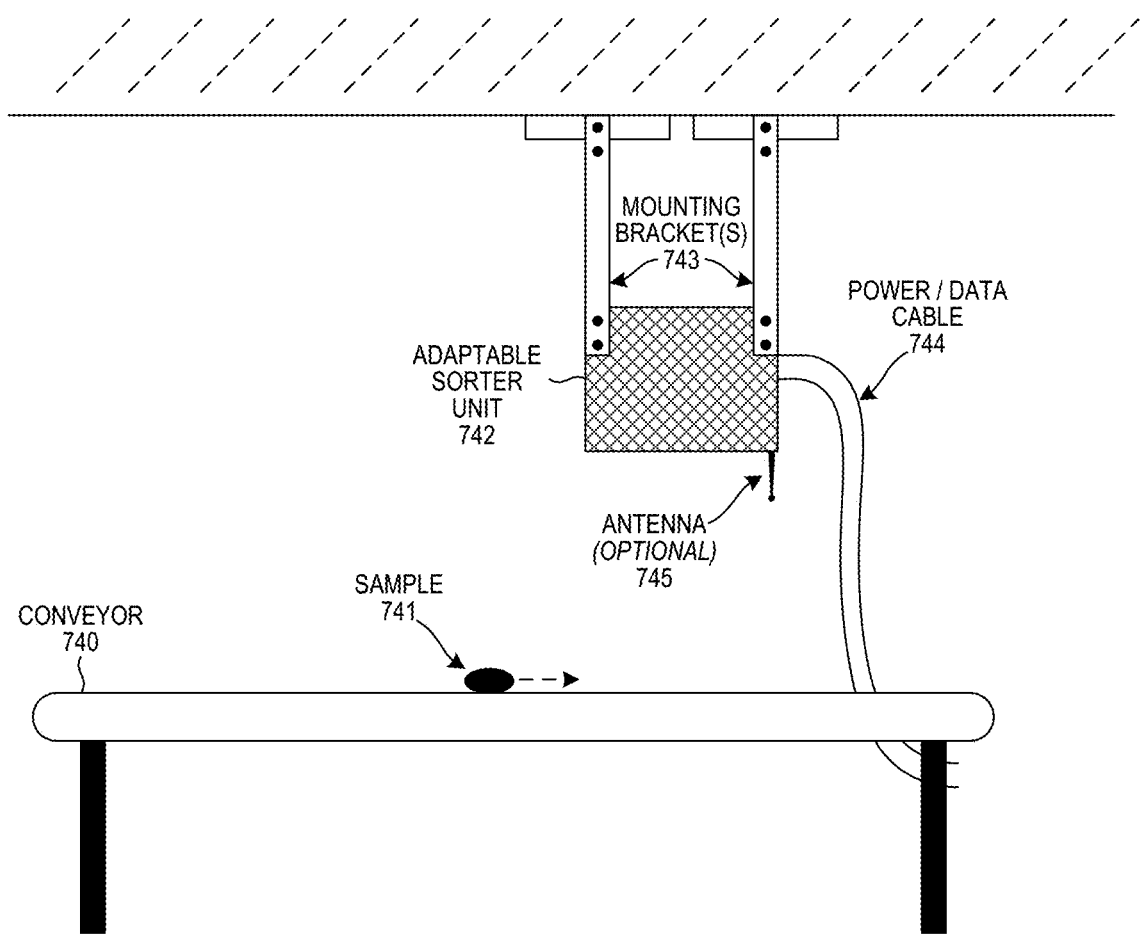
FIG. 34 is a diagram of a conveyor with an adaptable sorting unit attached to a ceiling above the conveyor.

FIG. 34 is a diagram of a conveyor with an adaptable sorting unit attached to a ceiling above the conveyor. Conveyor 740 is the same as conveyor 700, except in that adaptable sorter unit 742 has been physically mounted to the ceiling above conveyor 740. Similar to FIG. 30, in operation, sample 741 is caused to become in contact with conveyor 740. Upon contact, sample 741 is moved via a rotating conveyor belt of conveyor 740. The friction between the sample and the rotating conveyor belt causes the sample to be move along the direction of the conveyor belt movement.

The adaptable sorter unit 742 is attached to the ceiling above conveyor 740 via one or more mounting brackets 743. One skilled in the art will readily realize that a various number of brackets and various styles of brackets can be used to mount the adaptable sorter unit 742 to the ceiling above conveyor 740. Mounting Bracket 743 can attach to either the adaptable sorter unit 742 or the ceiling above conveyor 740 using various items, such as bolts, screws, pins, locks, clamps, welds (metals or thermoplastics), adhesive, slots, magnets, rails, gravity or friction.

The adaptable sorter unit 742 includes an attachment mechanism, a sorting device is capable of deflecting a sample, a data port and a power port. The data port and the power port may be combined into a single physical port that connects to a single cable 744 that includes both power conductors and data conductors. Alternatively, the adaptable sorter unit 742 may include a data port that is separate from the power port. Further, the adaptable sorter unit 742 may include an antenna connectable data port that connects to an antenna 745 so to allow for wireless communication. FIG. 34 does not illustrate the sorting device. FIG. 40 illustrates a block diagram of an adaptable sorter unit 800 that includes an attachment mechanism 801, a sorting device 802, a data port 803, and a power port 804.

In operation, the conveyor 740 causes the sample 741 to travel under the adaptable sorter unit 742. While the sample is in reach of the sorting device that is included in the adaptable sorter unit 742 the sample is sorted as instructed. In one example, the sorting instruction is received via the data port and stored in a memory included in the adaptable sorting unit 742. In another example, quality characteristic data is received via the data port and in response the adaptable sorter unit 742 generates the sorting instruction. In yet another example, the information received via the data port is a percentage of samples to be deflected. Communication with the adaptable sorter unit 742 may be performed via the data port (wired or wireless). The sorting device may be a vacuum system, a mechanical pedal system, an air jet system, or a mechanical gate. The adaptable sorting unit 742 performs automated sorting so that high quality samples are automatically separated from low quality samples.

Adaptable sorter unit 742 provides improve sorting compared to unreliable sorting by human hands without the cost of replacing an entire processing line. Moreover, adaptable sorter unit 742 is able to sort many more samples per unit time than could be sorted by a human.

Figure 35:
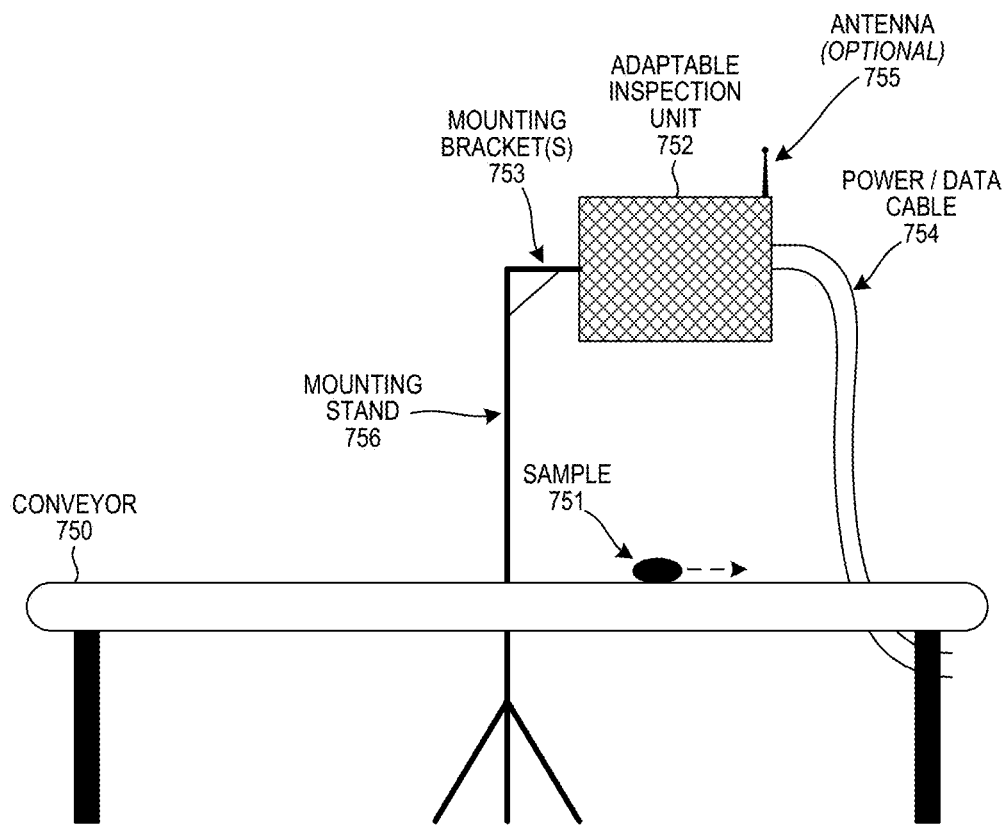
FIG. 35 is a diagram of a conveyor with an adaptable inspection unit attached to a mounting stand.

FIG. 35 is a diagram of a conveyor with an adaptable inspection unit attached to a mounting stand. Conveyor 750 is the same as conveyor 700, except in that adaptable inspection unit 752 has been physically mounted to a mounting stand 756 located next to conveyor 750. Similar to FIG. 30, in operation, sample 751 is caused to become in contact with conveyor 750. Upon contact, sample 751 is moved via a rotating conveyor belt of conveyor 750. The friction between the sample and the rotating conveyor belt causes the sample to be move along the direction of the conveyor belt movement.

The adaptable inspection unit 752 is attached to the mounting stand 756, located next to conveyor 750, via one or more mounting brackets 753. One skilled in the art will readily realize that a various number of brackets and various styles of brackets can be used to mount the adaptable inspection unit 752 to the mounting stand 756. Mounting Bracket 753 can attach to either the adaptable inspection unit 752 or the mounting stand 756 using various items, such as bolts, screws, pins, locks, clamps, welds (metals or thermoplastics), adhesive, slots, magnets, rails, gravity or friction.

The adaptable inspection unit 752 includes an attachment mechanism, an inspection sensor device (e.g. optical receiver), a data port and a power port. The data port and the power port may be combined into a single physical port that connects to a single cable 754 that includes both power conductors and data conductors. Alternatively, the adaptable inspection unit 752 may include a data port that is separate from the power port. Further, the adaptable inspection unit 752 may include an antenna connectable data port that connects to an antenna 755 so to allow for wireless communication. FIG. 35 does not illustrate the inspection sensor device. FIG. 39 illustrates a block diagram of an adaptable inspection unit 790 that includes an attachment mechanism 791, an inspection sensor device 792, a data port 793, and a power port 794.

In operation, the conveyor 750 causes the sample 751 to travel under the adaptable inspection unit 752. While the sample is in view, or reach, of the inspection sensor device that is included in the adaptable inspection unit 752 one or more characteristics and/or images of the sample are captured and stored in a memory device. The memory device may be included in the adaptable inspection unit 752 or may be included in a device that communicates with the adaptable inspection unit 752 via the data port (wired or wireless). The captured characteristics and/or image(s) are then processed by a processor executing a quality inspection algorithm. In one example, the adaptable inspection unit 752 includes the 3D inspector described in detail above. In another example, a 3D image of the sample is generated based on the one or more images captured by the adaptable inspection unit 752. In yet another example, the captured 2D image is used to perform the inspection. The 3D and/or 2D image(s) are used to determine a quality characteristic of the sample. In one example, the quality characteristic is generated by the adaptable inspection unit 752 and output via the data port. In another example, the one or more captured images are output from the adaptable inspection unit 752 to another device that determines the quality characteristics of the sample. Adaptable inspection unit 752 provides improve quality inspection compared to unreliable inspection by human eyes without the cost of replacing an entire processing line. Moreover, adaptable inspection unit 752 is able to inspect many more samples per unit time than could be inspected by a human.

In the example of FIG. 35, all samples are directed toward the same location regardless of measured quality because there is no sorting functionality attached to the conveyor 750.

Figure 36:
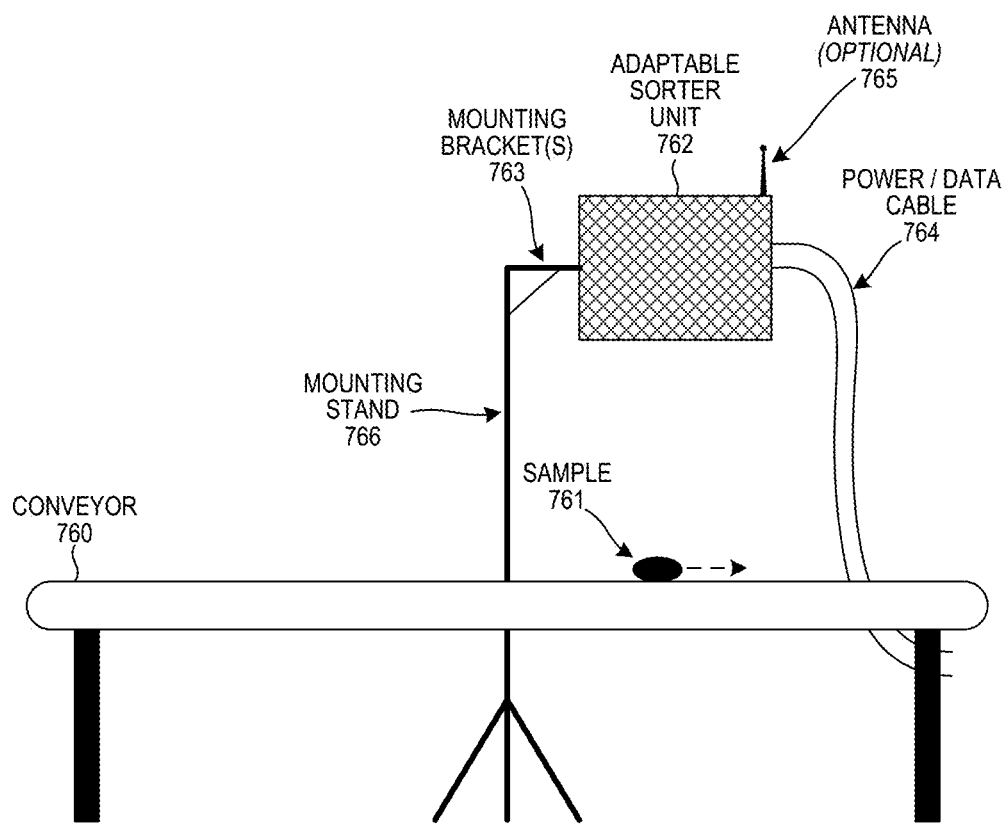
FIG. 36 is a diagram of a conveyor with an adaptable sorting unit attached to a mounting stand.

FIG. 36 is a diagram of a conveyor with an adaptable sorting unit attached to a mounting stand. Conveyor 760 is the same as conveyor 700, except in that adaptable sorter unit 762 has been physically mounted to a mounting stand 766 located next to conveyor 760. Similar to FIG. 30, in operation, sample 761 is caused to become in contact with conveyor 760. Upon contact, sample 761 is moved via a rotating conveyor belt of conveyor 760. The friction between the sample and the rotating conveyor belt causes the sample to be move along the direction of the conveyor belt movement.

The adaptable sorter unit 762 is attached to the mounting stand 766, located next to conveyor 760, via one or more mounting brackets 763. One skilled in the art will readily realize that a various number of brackets and various styles of brackets can be used to mount the adaptable sorter unit 762 to the mounting stand 766. Mounting Bracket 763 can attach to either the adaptable sorter unit 762 or the mounting stand 766 using various items, such as bolts, screws, pins, locks, clamps, welds (metals or thermoplastics), adhesive, slots, magnets, rails, gravity or friction.

The adaptable sorter unit 762 includes an attachment mechanism, a sorting device is capable of deflecting a sample, a data port and a power port. The data port and the power port may be combined into a single physical port that connects to a single cable 764 that includes both power conductors and data conductors. Alternatively, the adaptable sorter unit 762 may include a data port that is separate from the power port. Further, the adaptable sorter unit 762 may include an antenna connectable data port that connects to an antenna 765 so to allow for wireless communication. FIG. 36 does not illustrate the sorting device. FIG. 40 illustrates a block diagram of an adaptable sorter unit 800 that includes an attachment mechanism 801, a sorting device 802, a data port 803, and a power port 804.

In operation, the conveyor 760 causes the sample 761 to travel under the adaptable sorter unit 762. While the sample is in reach of the sorting device that is included in the adaptable sorter unit 762 the sample is sorted as instructed. In one example, the sorting instruction is received via the data port and stored in a memory included in the adaptable sorting unit 762. In another example, quality characteristic data is received via the data port and in response the adaptable sorter unit 762 generates the sorting instruction. In yet another example, the information received via the data port is a percentage of samples to be deflected. Communication with the adaptable sorter unit 762 may be performed via the data port (wired or wireless). The sorting device may be a vacuum system, a mechanical pedal system, an air jet system, or a mechanical gate. The adaptable sorting unit 762 performs automated sorting so that high quality samples are automatically separated from low quality samples.

Adaptable sorter unit 762 provides improve sorting compared to unreliable sorting by human hands without the cost of replacing an entire processing line. Moreover, adaptable sorter unit 762 is able to sort many more samples per unit time than could be sorted by a human.

Figure 37:
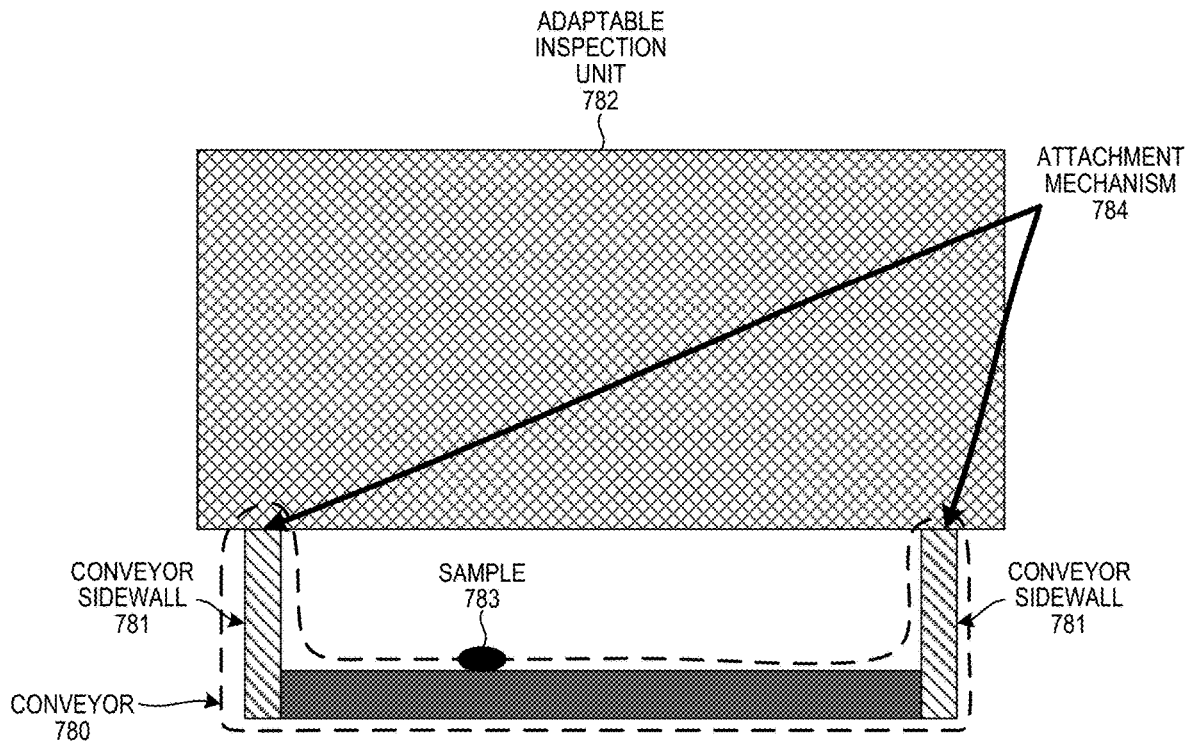
FIG. 37 is a diagram of a conveyor with an adaptable inspection unit attached to the conveyor sidewall. The adaptable inspection unit can be attached permanently or temporarily to the conveyor sidewall.

FIG. 37 is a diagram of a conveyor with an adaptable inspection unit attached to the conveyor sidewall. The adaptable inspection unit can be attached permanently or temporarily to the conveyor sidewall. Conveyor 780 includes one or more sidewalls 781 and a belt that rotates about two or more pulleys. The sidewall 781 is included in the conveyor 780 so to prevent samples from fall off the sides of the conveyor 780. The sidewall 781 of the conveyor 780 can be used to support the adaptable inspection unit 782. Although not shown in FIG. 37, the sidewall 781 can also be used to mount an adaptable sorter unit.

The adaptable inspection unit 782 (or an adaptable sorter unit) can be attached using many different mechanisms. Some of these mechanisms are listed on FIG. 37. These attachment mechanisms include welding the adaptable inspection unit 782 to the conveyor sidewall 781, gluing the adaptable inspection unit 782 to the conveyor sidewall 781, clamping the adaptable inspection unit 782 to the conveyor sidewall 781, magnetically attracting the adaptable inspection unit 782 to the conveyor sidewall 781, latching the adaptable inspection unit 782 to the conveyor sidewall 781, locking the adaptable inspection unit 782 to the conveyor sidewall 781, location pinning the adaptable inspection unit 782 to the conveyor sidewall 781, rail mating the adaptable inspection unit 782 to the conveyor sidewall 781, slide fitting the adaptable inspection unit 782 to the conveyor sidewall 781, lock pinning the adaptable inspection unit 782 to the conveyor sidewall 781, or using gravity and friction to "attach" the adaptable inspection unit 782 to the conveyor sidewall 781.

The adaptable inspection unit 782 includes an attachment mechanism, an inspection sensor device (e.g. an optical receiver), a data port and a power port. The data port and the power port may be combined into a single physical port that connects to a single cable 784 that includes both power conductors and data conductors. Alternatively, the adaptable inspection unit 782 may include a data port that is separate from the power port. Further, the adaptable inspection unit 782 may include an antenna connectable data port that connects to an antenna 785 so to allow for wireless communication. FIG. 37 does not illustrate the inspection sensor device. FIG. 39 illustrates a block diagram of an adaptable inspection unit 790 that includes an attachment mechanism 791, an inspection sensor device 792, a data port 793, and a power port 794.

In operation, the conveyor 780 causes the sample 781 to travel under the adaptable inspection unit 782. While the sample is in view, or reach, of the inspection sensor device that is included in the adaptable inspection unit 782 one or more characteristics and/or images of the sample are captured and stored in a memory device. The memory device may be included in the adaptable inspection unit 782 or may be included in a device that communicates with the adaptable inspection unit 782 via the data port (wired or wireless). The captured characteristics and/or image(s) are then processed by a processor executing a quality inspection algorithm. In one example, the adaptable inspection unit 782 includes the 3D inspector described in detail above. In another example, a 3D image of the sample is generated based on the one or more images captured by the adaptable inspection unit 782. In yet another example, the captured 2D image is used to perform the inspection. The 3D and/or 2D image(s) are used to determine a quality characteristic of the sample. In one example, the quality characteristic is generated by the adaptable inspection unit 782 and output via the data port. In another example, the one or more captured images are output from the adaptable inspection unit 782 to another device that determines the quality characteristics of the sample. Adaptable inspection unit 782 provides improve quality inspection compared to unreliable inspection by human eyes without the cost of replacing an entire processing line. Moreover, adaptable inspection unit 782 is able to inspect many more samples per unit time than could be inspected by a human.

In the example of FIG. 37, all samples are directed toward the same location regardless of measured quality because there is no sorting functionality attached to the conveyor 780. However, an adaptable sorer unit as described above could be placed further down the conveyor 780 to provide sorting functionality as well as inspection functionality.

Figure 38:
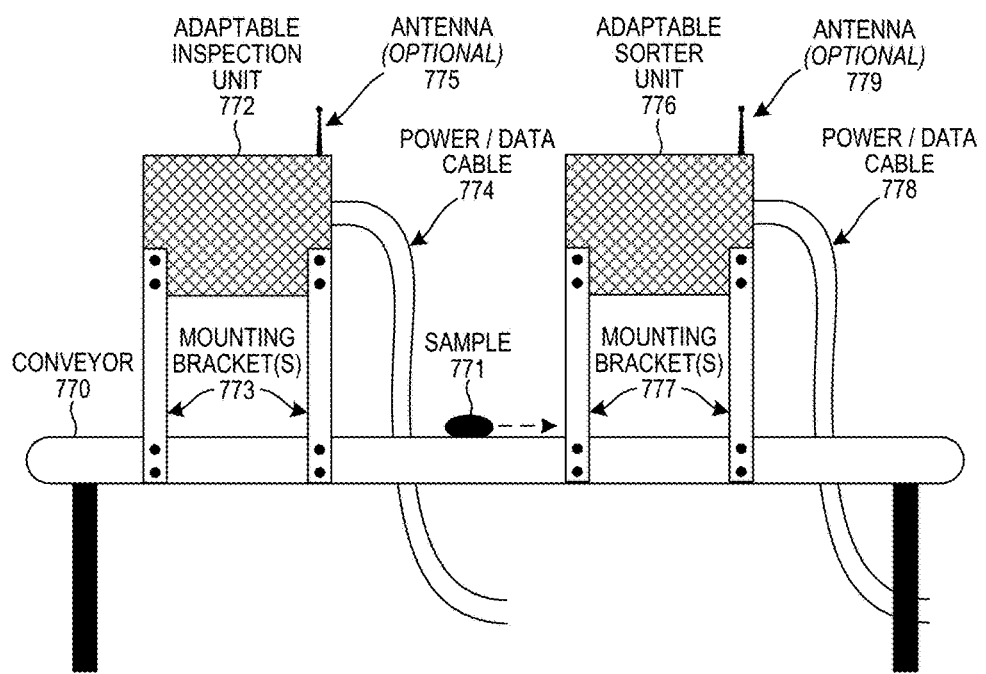
FIG. 38 is a diagram of a conveyor with an adaptable inspection unit attached to the conveyor and an adaptable sorting unit attached to the conveyor.

FIG. 38 is a diagram of a conveyor with an adaptable inspection unit attached to the conveyor and an adaptable sorting unit attached to the conveyor. As discussed above an adaptable inspection unit 772 and an adaptable sorter unit 776 can be mounted or positioned near an existing processing line. With these solutions, both an adaptable inspection unit 772 and an adaptable sorter unit 776 can be added to an existing processing line to allow for both automated quality inspection of samples as well as automated sorting of samples, without the cost of replacing the entire processing line. As discussed above, the adaptable inspection unit 772 and the adaptable sorter unit 776 can communicate with each other in various methods to achieve the desired inspection and sorting functions. Further, the adaptable inspection unit 772 and the adaptable sorter unit 776 can communicate with each in addition to a separate computing device, such as a network server to achieve the desired inspection and sorting functions. The drawings and related disclosure regarding FIGS. 14-27 illustrate and describe multiple methods in which the adaptable inspection unit 772 and the adaptable sorter unit 776 can communicate with each other in various methods to achieve the desired inspection and sorting functions (the adaptable inspection unit 772 performing the functions of the inspection device and the adaptable sorter unit 776 performing the functions of a slave device).

FIG. 39 is a block diagram of an adaptable inspection unit. The adaptable inspection unit 790 that includes an attachment mechanism 791, an inspection sensor device (optical receiver) 792, a data port 793, and a power port 794. The adaptable inspection unit 790 may also include a memory unit and a processor capable of controlling the inspection sensor device and writing information transmitted via the data port.

FIG. 40 is a block diagram of an adaptable sorter unit. The adaptable sorter unit 800 that includes an attachment mechanism 801, a sorting device 802, a data port 803, and a power port 804. The adaptable sorter unit 800 may also include a memory and a processor capable of reading information received via the data port and controlling the sorting device.

Figure 41:
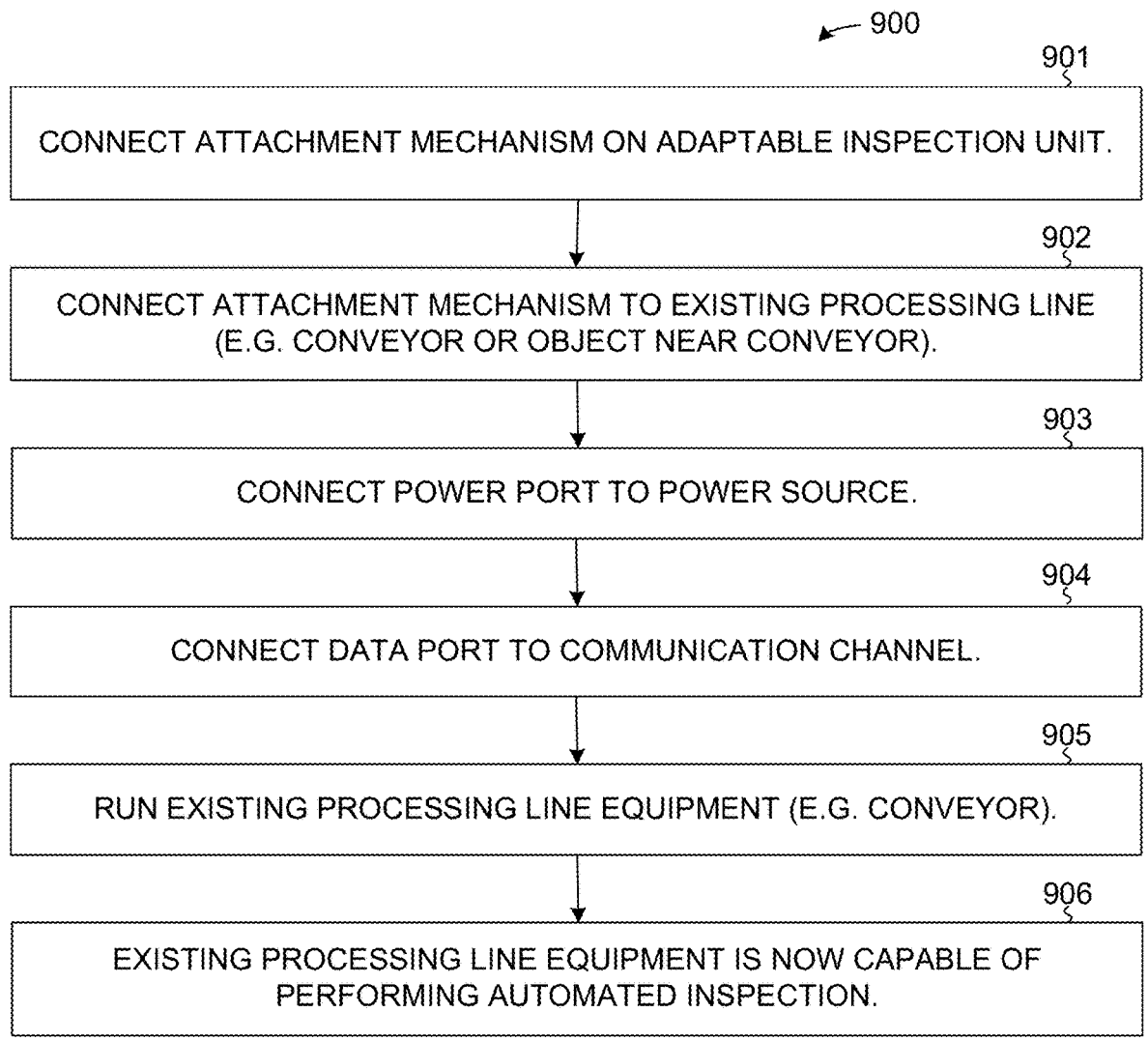
FIG. 41 is a flowchart illustrating the operations performed by an adaptable inspection unit.

FIG. 41 is a flowchart 900 illustrating the operations performed by an adaptable inspection unit. In step 901, an attachment mechanism is connected to the adaptable inspection unit. In step 902, the attachment mechanism is connected to the existing processing line. This can be a connection directly to the existing processing line or to an object near the existing processing line, such as a wall, ceiling, mounting stand, or conveyor sidewall. In step 903, a power port of the adaptable inspection unit is connected to a power source. In step 904, a data port of the adaptable inspection unit is connected to a data communication channel. The data communication channel can be a wired or wireless channel. In step 905, the existing processing line is run with the adaptable inspection unit in place and executing. In step 906, the existing processing line equipment is capable of performing automated inspection.

Figure 42:
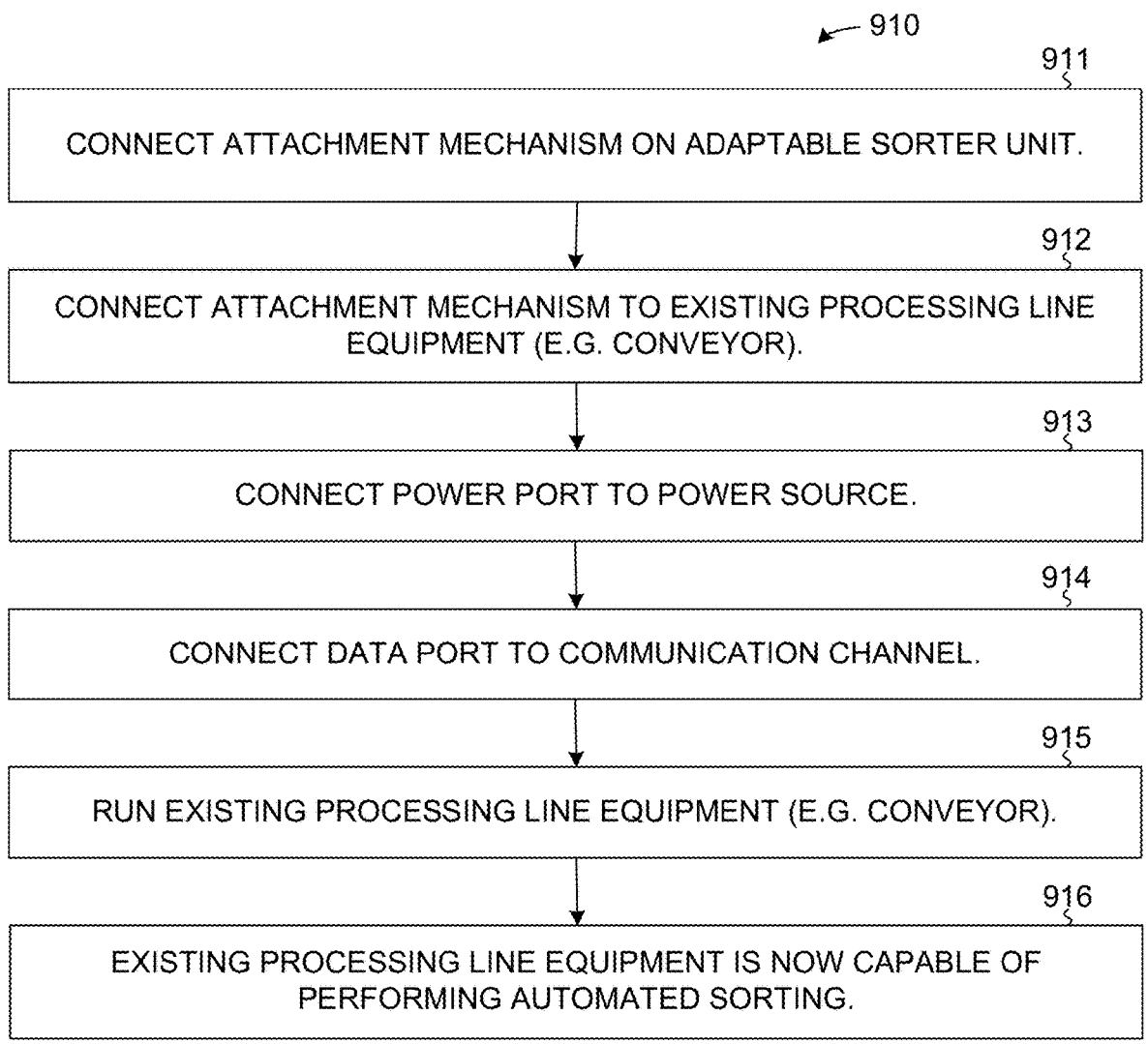
FIG. 42 is a flowchart illustrating the operations performed by an adaptable sorting unit.

FIG. 42 is a flowchart 910 illustrating the operations performed by an adaptable sorting unit. In step 911, an attachment mechanism is connected to the adaptable sorter unit. In step 912, the attachment mechanism is connected to the existing processing line. This can be a connection directly to the existing processing line or to an object near the existing processing line, such as a wall, ceiling, mounting stand, or conveyor sidewall. In step 913, a power port of the adaptable sorter unit is connected to a power source. In step 914, a data port of the adaptable sorter unit is connected to a data communication channel. The data communication channel can be a wired or wireless channel. In step 915, the existing processing line is run with the adaptable sorter unit in place and executing. In step 916, the existing processing line equipment is capable of performing automated sorting.

Given the new methods and apparatuses disclosed above, an existing processing line can be quickly and inexpensively retrofitted to perform automated inspection and automated sorting, which results in (i) improved inspection quality and reliability, (ii) improved sorting accuracy and reliability, (iii) improved throughput capability, and (iv) reduced operating costs.

The exemplary embodiments described above discuss adaptable inspection units and adaptable sorter units attached to a conveyor. However, one skilled in the art will readily appreciate that the adaptable inspection units and adaptable sorter units may also be attached to any other type of existing processing line, such as a chute in a similar manner to attain similar functionality and benefits.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:
1. An adaptable inspection unit, comprising:
an attachment mechanism that includes: a mounting bracket, a mounting bracket receptacle, a weldable material, a clamp, an adhesive, a magnet, a latch, a lock, a locating pin, a rail, a slide, locking pin, a bolt, or a screw;
an inspection sensor device;
a data port that is capable of transmitting information; and
a power port that is connectable to a power source, wherein the attachment mechanism, the inspection sensor device, the data port, and the power port are physically connected together such that the adaptable inspection unit is capable of capturing an image of a sample traveling along a processing line, wherein the processing line is a conveyor, and wherein the adaptable inspection unit is located above the conveyor when attached or proximate to the beginning of the conveyor when attached.

2. The adaptable inspection unit of claim 1, further comprising:
a memory circuit; and
a processor circuit adapted to:
control the inspection sensor device; and
cause information to be transmitted via the data port.

3. The adaptable inspection unit of claim 1, wherein the attachment mechanism affixes the adaptable inspection unit to a location proximate to processing line such that the adaptable inspection unit is capable of capturing an image of a sample traveling along the processing line.

4. The adaptable inspection unit of claim 1, wherein the adaptable inspection unit communicates with a sorting device via the data port.

5. The adaptable inspection unit of claim 4, wherein the data port is a wired communication port or a wireless communication port.

6. The adaptable inspection unit of claim 4, wherein the information transmitted by the adaptable inspection unit causes a mode of operation of the sorting device to be performed.

7. The adaptable inspection unit of claim 1, wherein the adaptable inspection unit outputs sample characterization data via the data port.

8. An adaptable inspection unit, comprising:
- an attachment mechanism that includes: a mounting bracket, a mounting bracket receptacle, a weldable material, a clamp, an adhesive, a magnet, a latch, a lock, a locating pin, a rail, a slide, locking pin, a bolt, or a screw;
- an inspection sensor device;
- a data port that is capable of transmitting information; and
- a power port that is connectable to a power source, wherein the attachment mechanism, the inspection sensor device, the data port, and the power port are physically connected together such that the adaptable inspection unit is capable of capturing an image of a sample traveling along a processing line, wherein the processing line is a chute, wherein the adaptable inspection unit is located above the chute when attached or proximate to the start of the chute when attached.

9. The adaptable inspection unit of claim 1, wherein the inspection sensor device includes an optical receiver.

10. The adaptable inspection unit of claim 1, wherein the inspection sensor device includes a plurality of optical receivers.

11. The adaptable inspection unit of claim 1, wherein the inspection sensor device includes a trigger to determine the presence of a sample.

12. The adaptable inspection unit of claim 1, wherein the information transmitted via the data port is a sorting command.

13. The adaptable inspection unit of claim 1, wherein the information transmitted via the data port is a sample characteristic data.

14. The adaptable inspection unit of claim 1, wherein the information transmitted via the data port is a percentage of samples to be deflected.

* * * * *